(12) United States Patent
van Deutekom

(10) Patent No.: US 7,534,879 B2
(45) Date of Patent: *May 19, 2009

(54) MODULATION OF EXON RECOGNITION IN PRE-MRNA BY INTERFERING WITH THE SECONDARY RNA STRUCTURE

(75) Inventor: Judith C. T. van Deutekom, Dordrecht (NL)

(73) Assignee: Academisch Ziekenhuis Leiden, Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/198,007

(22) Filed: Aug. 25, 2008

(65) Prior Publication Data

US 2009/0076246 A1 Mar. 19, 2009

Related U.S. Application Data

(63) Continuation of application No. 11/233,495, filed on Sep. 21, 2005, which is a continuation of application No. PCT/NL2003/000214, filed on Mar. 21, 2003.

(51) Int. Cl.
*C07H 21/04* (2006.01)
(52) U.S. Cl. .................. 536/24.5; 536/24.31; 435/6; 435/325; 435/375; 514/44
(58) Field of Classification Search .................. None
See application file for complete search history.

(56) References Cited

FOREIGN PATENT DOCUMENTS

| EP | 1 054 058 A1 | 5/2000 |
|---|---|---|
| EP | 1 133 993 A2 | 9/2001 |
| EP | 1 191 097 A1 | 3/2002 |
| WO | 2004/083432 A1 | 9/2004 |

OTHER PUBLICATIONS

Aartsma-Rus et al., Targeted exon skipping as a potential gene correction therapy for Duchenne muscular dystrophy, Neuromuscular Disorders, 2002, S71-S77, vol. 12.
Dickson et al., Screening for antisense modulation of dystrophin pre-mRNA splicing, Neuromuscul. Disord., 2002, S67-70, Suppl. 1.
De Angelis et al., Chimeric snRNA molecules carrying antisense sequences against the splice junctions of exon 51 of the dystrophin pre-mRNA induce exon skipping and restoration of a dystrophin synthesis in delta 48-50 DMD cells, PNAS, Jul. 9, 2002, pp. 9456-9461, vol. 99, No. 14.
Dunckley et al., Modifications of splicing in the dystrophin gene in cultured Mdx muscle cells by antisense oligoribonucleotides, Human Molecular Genetics, 1995, pp. 1083-1090, vol. 5, No. 1.
Lu et al., Massive Idiosyncratic Exon Skipping Corrects the Nonsense Mutation in Dystrophic Mouse Muscle and Produces Functional Revertant Fibers by Clonal Expansion, The Journal of Cell Biology, Mar. 6, 2000, pp. 985-995, vol. 148, No. 5.
Mann et al., Antisense-induced exon skipping and synthesis of dystrophin in the mdx mouse, PNAS, Jan. 2, 2001, pp. 42-47, vol. 98, No. 1.
Mann et al., Improved antisense oligonucleotide induced exon skipping in the mdx mouse model of muscular dystrophy, The Journal of Gene Medicine, 2002, pp. 644-654, vol. 4.
Suter et al., Double-target antisense U7 snRNAs promote efficient skipping of an aberrant exon in three human B-thalassemic mutations, Human Molecular Genetics, 1999, pp. 2415-2423, vol. 8, No. 13.
Van Deutekom et al., Antisense-induced exon skipping restores dystrophin expression in DMD patient derived muscle cells, Human Molecular Genetics, 2001, pp. 1547-1554, vol. 10, No. 15.

*Primary Examiner*—Kimberly Chong
(74) *Attorney, Agent, or Firm*—TraskBritt

(57) ABSTRACT

The invention provides a method for generating an oligonucleotide with which an exon may be skipped in a pre-mRNA and thus excluded from a produced mRNA thereof. Further provided are methods for altering the secondary structure of an mRNA to interfere with splicing processes and uses of the oligonucleotides and methods in the treatment of disease. Further provided are pharmaceutical compositions and methods and means for inducing skipping of several exons in a pre-mRNA.

3 Claims, 7 Drawing Sheets

A

B

SEQUENCE LISTING

```
<160> NUMBER OF SEQ ID NOS: 30

<210> SEQ ID NO 1
<211> LENGTH: 24
<212> TYPE: RNA
<213> ORGANISM: Artificial Sequence
<220> FEATURE:
<223> OTHER INFORMATION: h2AON1

<400> SEQUENCE: 1
cccauuuugu gaauguuuuc uuuu                                          24

<210> SEQ ID NO 2
<211> LENGTH: 22
<212> TYPE: RNA
<213> ORGANISM: Artificial Sequence
<220> FEATURE:
<223> OTHER INFORMATION: h2AON2

<400> SEQUENCE: 2
uugugcauuu acccauuuug ug                                            22
```

```
<210> SEQ ID NO 3
<211> LENGTH: 20
<212> TYPE: RNA
<213> ORGANISM: Artificial Sequence
<220> FEATURE:
<223> OTHER INFORMATION: h29AON1

<400> SEQUENCE: 3
uauccucuga augucgcauc                                                     20

<210> SEQ ID NO 4
<211> LENGTH: 20
<212> TYPE: RNA
<213> ORGANISM: Artificial Sequence
<220> FEATURE:
<223> OTHER INFORMATION: h29AON2

<400> SEQUENCE: 4
gguuauccuc ugaaugucgc                                                     20

<210> SEQ ID NO 5
<211> LENGTH: 19
<212> TYPE: RNA
<213> ORGANISM: Artificial Sequence
<220> FEATURE:
<223> OTHER INFORMATION: h40AON1

<400> SEQUENCE: 5
gagccuuuuu ucuucuuug                                                      19

<210> SEQ ID NO 6
<211> LENGTH: 19
<212> TYPE: RNA
<213> ORGANISM: Artificial Sequence
<220> FEATURE:
<223> OTHER INFORMATION: h40AON2

<400> SEQUENCE: 6
uccuuucguc ucugggcuc                                                      19

<210> SEQ ID NO 7
<211> LENGTH: 19
<212> TYPE: RNA
<213> ORGANISM: Artificial Sequence
<220> FEATURE:
<223> OTHER INFORMATION: h41AON1

<400> SEQUENCE: 7
cuccucuuuc uucuucugc                                                      19

<210> SEQ ID NO 8
<211> LENGTH: 20
<212> TYPE: RNA
<213> ORGANISM: Artificial Sequence
<220> FEATURE:
<223> OTHER INFORMATION: h41AON2

<400> SEQUENCE: 8
cuucgaaacu gagcaaauuu                                                     20

<210> SEQ ID NO 9
<211> LENGTH: 17
<212> TYPE: RNA
<213> ORGANISM: Artificial Sequence
<220> FEATURE:
<223> OTHER INFORMATION: h42AON1
```

-continued

```
<400> SEQUENCE: 9
cuugugagac augagug                                                    17

<210> SEQ ID NO 10
<211> LENGTH: 18
<212> TYPE: RNA
<213> ORGANISM: Artificial Sequence
<220> FEATURE:
<223> OTHER INFORMATION: h42AON2

<400> SEQUENCE: 10
cagagacucc ucuugcuu                                                   18

<210> SEQ ID NO 11
<211> LENGTH: 18
<212> TYPE: RNA
<213> ORGANISM: Artificial Sequence
<220> FEATURE:
<223> OTHER INFORMATION: h43AON1

<400> SEQUENCE: 11
ugcugcuguc uucuugcu                                                   18

<210> SEQ ID NO 12
<211> LENGTH: 19
<212> TYPE: RNA
<213> ORGANISM: Artificial Sequence
<220> FEATURE:
<223> OTHER INFORMATION: h43AON2

<400> SEQUENCE: 12
uuguuaacuu uuucccauu                                                  19

<210> SEQ ID NO 13
<211> LENGTH: 19
<212> TYPE: RNA
<213> ORGANISM: Artificial Sequence
<220> FEATURE:
<223> OTHER INFORMATION: h44AON1

<400> SEQUENCE: 13
cgccgccauu ucucaacag                                                  19

<210> SEQ ID NO 14
<211> LENGTH: 20
<212> TYPE: RNA
<213> ORGANISM: Artificial Sequence
<220> FEATURE:
<223> OTHER INFORMATION: h44AON2

<400> SEQUENCE: 14
uuuguauuua gcauguuccc                                                 20

<210> SEQ ID NO 15
<211> LENGTH: 19
<212> TYPE: RNA
<213> ORGANISM: Artificial Sequence
<220> FEATURE:
<223> OTHER INFORMATION: h45AON1

<400> SEQUENCE: 15
gcugaauuau uucuucccc                                                  19

<210> SEQ ID NO 16
<211> LENGTH: 17
```

```
<212> TYPE: RNA
<213> ORGANISM: Artificial Sequence
<220> FEATURE:
<223> OTHER INFORMATION: h45AON5

<400> SEQUENCE: 16
gcccaaugcc auccugg                                                17

<210> SEQ ID NO 17
<211> LENGTH: 15
<212> TYPE: RNA
<213> ORGANISM: Artificial Sequence
<220> FEATURE:
<223> OTHER INFORMATION: h46AON4b

<400> SEQUENCE: 17
cugcuuccuc caacc                                                  15

<210> SEQ ID NO 18
<211> LENGTH: 20
<212> TYPE: RNA
<213> ORGANISM: Artificial Sequence
<220> FEATURE:
<223> OTHER INFORMATION: h46AON8b

<400> SEQUENCE: 18 gcuuucuuu uaguugcugc                                              20

<210> SEQ ID NO 19
<211> LENGTH: 18
<212> TYPE: RNA
<213> ORGANISM: Artificial Sequence
<220> FEATURE:
<223> OTHER INFORMATION: h47AON1

<400> SEQUENCE: 19
ucuugcucuu cugggcuu                                               18

<210> SEQ ID NO 20
<211> LENGTH: 21
<212> TYPE: RNA
<213> ORGANISM: Artificial Sequence
<220> FEATURE:
<223> OTHER INFORMATION: h47AON2

<400> SEQUENCE: 20
cuugagcuua uuucaaguu u                                            21

<210> SEQ ID NO 21
<211> LENGTH: 16
<212> TYPE: RNA
<213> ORGANISM: Artificial Sequence
<220> FEATURE:
<223> OTHER INFORMATION: h48AON1

<400> SEQUENCE: 21
uuucuccuug uuucuc                                                 16

<210> SEQ ID NO 22
<211> LENGTH: 21
<212> TYPE: RNA
<213> ORGANISM: Artificial Sequence
<220> FEATURE:
<223> OTHER INFORMATION: h48AON2

<400> SEQUENCE: 22
```

-continued

| ccauaaauuu ccaacugauu c | 21 |

```
<210> SEQ ID NO 23
<211> LENGTH: 19
<212> TYPE: RNA
<213> ORGANISM: Artificial Sequence
<220> FEATURE:
<223> OTHER INFORMATION: h49AON1

<400> SEQUENCE: 23
```

| cuuccacauc cgguuguuu | 19 |

```
<210> SEQ ID NO 24
<211> LENGTH: 19
<212> TYPE: RNA
<213> ORGANISM: Artificial Sequence
<220> FEATURE:
<223> OTHER INFORMATION: h49AON2

<400> SEQUENCE: 24
```

| guggcugguu uuccuugu | 19 |

```
<210> SEQ ID NO 25
<211> LENGTH: 17
<212> TYPE: RNA
<213> ORGANISM: Artificial Sequence
<220> FEATURE:
<223> OTHER INFORMATION: h50AON1

<400> SEQUENCE: 25
```

| cucagagcuc agaucuu | 17 |

```
<210> SEQ ID NO 26
<211> LENGTH: 15
<212> TYPE: RNA
<213> ORGANISM: Artificial Sequence
<220> FEATURE:
<223> OTHER INFORMATION: h50AON2

<400> SEQUENCE: 26
```

| ggcugcuuug cccuc | 15 |

```
<210> SEQ ID NO 27
<211> LENGTH: 20
<212> TYPE: RNA
<213> ORGANISM: Artificial Sequence
<220> FEATURE:
<223> OTHER INFORMATION: h51AON1

<400> SEQUENCE: 27
```

| ucaaggaaga uggcauuucu | 20 |

```
<210> SEQ ID NO 28
<211> LENGTH: 23
<212> TYPE: RNA
<213> ORGANISM: Artificial Sequence
<220> FEATURE:
<223> OTHER INFORMATION: h51AON2

<400> SEQUENCE: 28
```

| ccucugugau uuuauaacuu gau | 23 |

```
<210> SEQ ID NO 29
<211> LENGTH: 18
<212> TYPE: RNA
<213> ORGANISM: Artificial Sequence
```

```
-continued

<220> FEATURE:
<223> OTHER INFORMATION: h53AON1

<400> SEQUENCE: 29
cguuugccuc cgguucug                                                        18

<210> SEQ ID NO 30
<211> LENGTH: 18
<212> TYPE: RNA
<213> ORGANISM: Artificial Sequence
<220> FEATURE:
<223> OTHER INFORMATION: h53AON2

<400> SEQUENCE: 30
uuggcucugg ccuguccu                                                        18
```

MODULATION OF EXON RECOGNITION IN PRE-MRNA BY INTERFERING WITH THE SECONDARY RNA STRUCTURE

CROSS-REFERENCE TO RELATED APPLICATIONS

This application is a continuation of patent application Ser. No. 11/233,495, filed Sep. 21, 2005, pending, which is a continuation of PCT International Patent Application No. PCT/NL2003/000214, filed on Mar. 21, 2003, designating the United States of America, and published, in English, as PCT International Publication No. WO 2004/083432 A1 on Sep. 30, 2004, the contents of the entirety of each of which is incorporated by this reference.

TECHNICAL FIELD

The invention relates to the fields of molecular biology and medicine. More in particular, the invention relates to the restructuring of mRNA produced from pre-mRNA, and therapeutic uses thereof.

BACKGROUND

The central dogma of biology is that genetic information resides in the DNA of a cell and is expressed upon transcription of this information, where after production of the encoded protein follows by the translation machinery of the cell. This view of the flow of genetic information has prompted the predominantly DNA-based approach for interfering with the protein content of a cell. This view is slowly changing and alternatives for interfering at the DNA level are being pursued.

In higher eukaryotes, the genetic information for proteins in the DNA of the cell is encoded in exons that are separated from each other by intronic sequences. These introns are in some cases very long. The transcription machinery generates a pre-mRNA that contains both exons and introns, while the splicing machinery, often already during the production of the pre-mRNA, generates the actual coding region for the protein by splicing together the exons present in the pre-mRNA.

Although much is known about the actual processes involved in the generation of an mRNA from a pre-mRNA, much also remains hidden. In the invention it has been shown possible to influence the splicing process such that a different mRNA is produced. The process allows for the predictable and reproducible restructuring of mRNA produced by a splicing machinery. An oligonucleotide capable of hybridizing to pre-mRNA at a location of an exon that is normally included in the mature mRNA can direct the exclusion of the thus targeted exon or a part thereof.

SUMMARY OF THE INVENTION

In the invention, means and methods are provided for the design of appropriate complementary oligonucleotides. To this end, the invention provides a method for generating an oligonucleotide comprising determining, from a (predicted) secondary structure of RNA from an exon, a region that assumes a structure that is hybridized to another part of the RNA (closed structure) and a region that is not hybridized in the structure (open structure), and subsequently generating an oligonucleotide, which at least in part is complementary to the closed structure and which at least in part is complementary to the open structure. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. Through its structure, an exon is recognized as a part that needs to be included in the pre-mRNA. Herein, this signaling function is referred to as an "exon inclusion signal." A complementary oligonucleotide of the invention is capable of interfering with the structure of the exon and thereby capable of interfering with the exon inclusion signal of the exon. It has been found that many complementary oligonucleotides indeed comprise this capacity, some more efficiently than others. Oligonucleotides of the invention, i.e., those with the overlap directed toward open and closed structures in the native exon RNA, are a selection from all possible oligonucleotides. The selection encompasses oligonucleotides that can efficiently interfere with an exon inclusion signal.

Without being bound by theory, it is thought that the overlap with an open structure improves the invasion efficiency of the oligonucleotide (i.e., increases the efficiency with which the oligonucleotide can enter the structure), whereas the overlap with the closed structure subsequently increases the efficiency of interfering with the secondary structure of the RNA of the exon, and thereby interfere with the exon inclusion signal. It is found that the length of the partial complementarity to both the closed and the open structure is not extremely restricted. We have observed high efficiencies with oligonucleotides with variable lengths of complementarity in either structure. The term "complementarity" is used herein to refer to a stretch of nucleic acids that can hybridize to another stretch of nucleic acids under physiological conditions. It is thus not absolutely required that all the bases in the region of complementarity are capable of pairing with bases in the opposing strand. For instance, when designing the oligonucleotide, one may want to incorporate, for example, a residue that does not base pair with the base on the complementary strand. Mismatches may to some extent be allowed, if under the circumstances in the cell, the stretch of nucleotides is capable of hybridizing to the complementary part. In a preferred embodiment, a complementary part (either to the open or to the closed structure) comprises at least three and, more preferably, at least four, consecutive nucleotides. The complementary regions are preferably designed such that, when combined, they are specific for the exon in the pre-mRNA. Such specificity may be created with various lengths of complementary regions as this depends on the actual sequences in other mRNA or pre-mRNA in the system. The risk that also one or more other pre-RNA will be able to hybridize to the oligonucleotide decreases with increasing size of the oligonucleotide. It is clear that oligonucleotides comprising mismatches in the region of complementarity but that retain the capacity to hybridize to the targeted region(s) in the pre-mRNA, can be used in the invention. However, preferably at least the complementary parts do not comprise such mismatches as these typically have a higher efficiency and a higher specificity, than oligonucleotides having such mismatches in one or more complementary regions. It is thought that higher hybridization strengths (i.e., increasing number of interactions with the opposing strand), are favorable in increasing the efficiency of the process of interfering with the splicing machinery of the system.

The secondary structure is best analyzed in the context of the pre-mRNA wherein the exon resides. Such structure may be analyzed in the actual RNA. However, it is currently possible to predict the secondary structure of an RNA molecule (at lowest energy costs) quite well using structure-modeling programs. A non-limiting example of a suitable program is RNA mfold version 3.1 server (Mathews et al., 1999, *J. Mol. Biol.* 288:911-940). A person skilled in the art will be able to predict, with suitable reproducibility, a likely structure of the exon, given the nucleotide sequence. Best predictions are obtained when providing such modeling programs with both the exon and flanking intron sequences. It is typically not necessary to model the structure of the entire pre-mRNA.

The open and closed structure to which the oligonucleotide is directed, are preferably adjacent to one another. It is thought that in this way, the annealing of the oligonucleotide to the open structure induces opening of the closed structure, and annealing progresses into this closed structure. Through this action, the previously closed structure assumes a different conformation. The different conformation may result in the disruption of the exon inclusion signal. However, when potential (cryptic) splice acceptor and/or donor sequences are present within the targeted exon, occasionally a new exon inclusion signal is generated defining a different (neo) exon, e.g., with a different 5' end, a different 3' end, or both. This type of activity is within the scope of the invention as the targeted exon is excluded from the mRNA. The presence of a new exon, containing part of the targeted exon, in the mRNA does not alter the fact that the targeted exon, as such, is excluded. The inclusion of a neo-exon can be seen as a side effect which occurs only occasionally. There are two possibilities when exon skipping is used to restore (part of) an open reading frame that was disrupted as a result of a mutation. One is that the neo-exon is functional in the restoration of the reading frame, whereas in the other case the reading frame is not restored. When selecting oligonucleotides for restoring reading frames by means of exon-skipping, it is, of course, clear that under these conditions, only those oligonucleotides are selected that indeed result in exon-skipping that restores the open reading frame, with or without a neo-exon.

Pre-mRNA can be subject to various splicing events, for instance, through alternative splicing. Such events may be induced or catalyzed by the environment of a cell or artificial splicing system. Thus, from the same pre-mRNA, several different mRNAs may be produced. The different mRNAs all included exonic sequences, as that is the definition of an exon. However, the fluidity of the mRNA content necessitates a definition of the term "exon" in the invention. An "exon," according to the invention, is a sequence present in both the pre-mRNA and mRNA produced thereof, wherein the sequence included in the mRNA is, in the pre-mRNA, flanked on one side (first and last exon) or both sides (any exon other than the first and the last exon) by sequences not present in the mRNA. In principle, any mRNA produced from the pre-mRNA qualifies for this definition. However, for the invention, so-called dominant mRNAs are preferred, i.e., mRNA that makes up at least 5% of the mRNA produced from the pre-mRNA under the set conditions. Human immuno-deficiency virus, in particular, uses alternative splicing to an extreme. Some very important protein products are produced from mRNA making up even less than 5% of the total mRNA produced from the virus. The genomic RNA of retroviruses can be seen as pre-mRNA for any spliced product derived from it. As alternative splicing may vary in different cell types, the exons are defined as exons in the context of the splicing conditions used in that system. As a hypothetical example, an mRNA in a muscle cell may contain an exon that is absent in an mRNA produced from the same pre-mRNA in a nerve cell. Similarly, mRNA in a cancer cell may contain an exon not present in mRNA produced from the same mRNA in a normal cell.

Alternative splicing may occur by splicing from the same pre-mRNA. However, alternative splicing may also occur through a mutation in the pre-mRNA, for instance, generating an additional splice acceptor and/or splice donor sequence. Such alternative splice sequences are often referred to as cryptic splice acceptor/donor sequences. Such cryptic splice sites can result in new exons (neo-exons). Inclusion of neo-exons into produced mRNA can be prevented, at least in part, using a method of the invention. In case a neo-exon is flanked by a cryptic and a "normal" splice donor/acceptor sequence, the neo-exon encompasses the old (paleo) exon. If in this case the original splice donor/acceptor sequence, for which the cryptic splice donor/acceptor has taken its place, is still present in the pre-mRNA, it is possible to enhance the production of mRNA containing the paleo-exon by interfering with the exon-recognition signal of the neo-exon. This interference can be both in the part of the neo-exon corresponding to the paleo-exon, or the additional part of such neo-exons. This type of exon skipping can be seen as splice correction.

The exon skipping technique can be used for many different purposes. Preferably, however, exon skipping is used for restructuring mRNA that is produced from pre-mRNA exhibiting undesired splicing in a subject. The restructuring may be used to decrease the amount of protein produced by the cell. This is useful when the cell produces a particular undesired protein. In a preferred embodiment, however, restructuring is used to promote the production of a functional protein in a cell, i.e., restructuring leads to the generation of a coding region for a functional protein. The latter embodiment is preferably used to restore an open reading frame that was lost as a result of a mutation. Preferred genes comprise a Duchenne muscular dystrophy gene, a collagen VI alpha 1 gene (COL6A1), a myotubular myopathy 1 gene (MTM1), a dysferlin gene (DYSF), a laminin-alpha 2 gene (LAMA2), an emery-dreyfuss muscular dystrophy gene (EMD), and/or a calpain 3 gene (CAPN3). The invention is further delineated by means of examples drawn from the Duchenne muscular dystrophy gene. Although this gene constitutes a particularly preferred gene in the invention, the invention is not limited to this gene.

Duchenne muscular dystrophy (DMD) and Becker muscular dystrophy (BMD) are both caused by mutations in the DMD gene that is located on the X chromosome and codes for dystrophin (1-6). DMD has an incidence of 1:3500 newborn males. Patients suffer from progressive muscle weakness, are wheelchair bound before the age of 13 and often die before the third decade of their life (7). The generally milder BMD has an incidence of 1:20,000. BMD patients often remain ambulant for over 40 years and have longer life expectancies when compared to DMD patients (8).

Dystrophin is an essential component of the dystrophin-glycoprotein complex (DGC), which, amongst others, maintains the membrane stability of muscle fibers (9, 10). Frame-shifting mutations in the DMD gene result in dystrophin deficiency in muscle cells. This is accompanied by reduced levels of other DGC proteins and results in the severe phenotype found in DMD patients (11, 12). Mutations in the DMD gene that keep the reading frame intact, generate shorter, but partly functional dystrophins, associated with the less severe BMD (13, 14).

Despite extensive efforts, no clinically applicable and effective therapy for DMD patients has yet been developed (15), although a delay of the onset and/or progression of disease manifestations can be achieved by glucocorticoid therapy (16). Promising results have recently been reported by us and others on a genetic therapy aimed at restoring the reading frame of the dystrophin pre-mRNA in cells from the mdx mouse model and DMD patients (17-23). By the targeted skipping of a specific exon, a DMD phenotype can be converted into a milder BMD phenotype. The skipping of an exon can be induced by the binding of antisense oligoribonucleotides ("AONs"), targeting either one or both of the splice sites or exon-internal sequences. Since an exon will only be included in the mRNA when both the splice sites are recognized by the spliceosome complex, splice sites are obvious targets for AONs. This was shown to be successful, albeit with variable efficacy and efficiency (17, 18, 20, 21).

We hypothesized that targeting exon-internal sequences might increase specificity and reduce interference with the splicing machinery itself. Some exons have weak splice sites and appear to require binding of an SR protein to an exon recognition sequence (ERS) or an exonic splicing enhancer (ESE) to be properly recognized by the splicing machinery (24). SR proteins are a highly conserved family of arginine-/serine-rich, spliceosome-associated phosphoproteins essential for pre-mRNA splicing (50, 51). SR proteins appear to act early in splicing by promoting splice site recognition and spliceosome assembly. SR proteins also play a regulatory role, because they can determine alternative splice site usage in vivo and in vitro. SR proteins appear to be recruited from nuclear "speckles" in which they are concentrated, to sites of transcription in order to spatially coordinate transcription and pre-mRNA splicing within the cell nucleus (49, 52). Disruptive point mutations or AONs that block these sequences have been found to result in exon skipping (19, 22, 24-28). Using exon-internal AONs specific for an ERS-like sequence in exon 46, we were previously able to modulate the splicing pattern in cultured myotubes from two different DMD patients with an exon 45 deletion (19). Following AON treatment, exon 46 was skipped, which resulted in a restored reading frame and the induction of dystrophin synthesis in at least 75% of the cells. We have recently shown that exon skipping can also efficiently be induced in human control muscle cells for 15 different DMD exons using exon-internal AONs (23, unpublished results).

In contrast to the previous opinion that skipping can only be achieved with weak splice sites or exons containing ERS-like sequences, we have seen that of the exons that were skipped in the invention, most do not have weak splice sites nor do they contain ERS-like sequences. Thus, binding of the AONs to the targeted exon per se is sufficient to cause exon skipping, either by interfering with one or more components of the splicing machinery or by altering the secondary structure of the RNA in such a manner that the splicing machinery no longer recognizes the exon. In a preferred embodiment, the exon to be skipped comprises exons 2, 8, 9, 17, 19, 29, 40-46, 49-53, 55 or 59; more preferably, exons 2, 8, 9, 17, 40, 41, 42, 44, 49-52 or 59. In yet another embodiment, the exon to be skipped comprises exons 2, 29, 40, 41, 42, 43, 44, 45, 46, 49, 50, 51 or 53.

Any oligonucleotide fulfilling the requirements of the invention may be used to induce exon skipping in the DMD gene. In a preferred embodiment, an oligonucleotide comprises a sequence as depicted as active in exon-skipping in Table 2, or a functional equivalent thereof comprising a similar, preferably the same, hybridization capacity in kind, not necessarily in amount. Preferably, an oligonucleotide comprising a sequence as depicted in Table 2, derived from the exons 2, 40, 41, 42, 43, 44, 45, 49, 50, 51 or 53, demonstrably active in exon skipping.

Reading frame correction can be achieved by skipping one or two exons flanking a deletion, by skipping in-frame exons containing a nonsense mutation, or by skipping duplicated exons. This results in proteins similar to those found in various BMD patients (2, 29). A survey of the Leiden DMD mutation database (WorldWideWeb.dmd.nl; (30)) evinces that we can thus correct over 75% of DMD-causing mutations (see Table 4). We show the actual therapeutic effect of exon skipping for seven different mutations. In all patient muscle cell cultures, we were able to restore dystrophin synthesis in 75% to 80% of treated cells.

The complementary oligonucleotide generated through a method of the invention is preferably complementary to a consecutive part of between 16 and 50 nucleotides of the exon RNA. Different types of nucleic acid may be used to generate the oligonucleotide. Preferably, the oligonucleotide comprises RNA, as RNA/RNA hybrids are very stable. Since one of the aims of the exon skipping technique is to direct splicing in subjects, it is preferred that the oligonucleotide RNA comprises a modification providing the RNA with an additional property, for instance, resistance to endonucleases and RNaseH, additional hybridization strength, increased stability (for instance, in a bodily fluid), increased or decreased flexibility, reduced toxicity, increased intracellular transport, and/or tissue-specificity, etc. Preferably, the modification comprises a 2'-O-methyl-phosphorothioate oligoribonucleotide modification.

With the advent of nucleic acid-mimicking technology, it has become possible to generate molecules that have a similar, preferably the same, hybridization characteristics, in kind, not necessarily in amount, as nucleic acid itself. Such equivalents are, of course, also part of the invention. Examples of such mimics equivalents are peptide nucleic acid, locked nucleic acid and/or a morpholino phosphorodiamidate. Suitable but non-limiting examples of equivalents of oligonucleotides of the invention can be found in C. Wahlestedt et al., Potent and non-toxic antisense oligonucleotides containing locked nucleic acids, *Proc. Natl. Acad. Sci. U.S.A.* 97:5633-8 (2000); A. N. Elayadi and D. R. Corey, Application of PNA and LNA oligomers to chemotherapy, *Curr. Opin. Investig. Drugs* 2:558-61 (2001); H. J. Larsen, T. Bentin, and P. E. Nielsen, Antisense properties of peptide nucleic acid, *Biochim. Biophys, Acta* 1489:159-66 (1999); D. A. Braasch and D. R. Corey, Novel antisense and peptide nucleic acid strategies for controlling gene expression, *Biochemistry* 41:4503-10 (2002); J. Summerton and D. Weller, Morpholino antisense oligomers: design, preparation, and properties, *Antisense Nucleic Acid Drug Dev.* 7:187-95 (1997). Hybrids between one or more of the equivalents among each other and/or together with nucleic acid are, of course, also part of the invention. In a preferred embodiment, an equivalent comprises locked nucleic acid, as locked nucleic acid displays a higher target affinity and reduced toxicity and, therefore, shows a higher efficiency of exon skipping.

An oligonucleotide of the invention typically does not have to overlap with a splice donor or splice acceptor of the exon.

An oligonucleotide of the invention, or equivalent thereof, may, of course, be combined with other methods for interfering with the structure of an mRNA. It is, for instance, possible to include in a method at least one other oligonucleotide that is complementary to at least one other exon in the pre-mRNA. This can be used to prevent inclusion of two or more exons of a pre-mRNA in mRNA produced from this pre-mRNA. In a preferred embodiment, at least one other oligonucleotide is an oligonucleotide, or equivalent thereof, generated through a method of the invention. This part of the invention is further referred to as double- or multi-exon skipping. In most cases, double-exon skipping results in the exclusion of only the two targeted (complementary) exons from the pre-mRNA. However, in other cases, it was found that the targeted exons and the entire region in between the exons in the pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

It has now also been found possible to specifically promote the skipping of the intervening exons by providing a linkage between the two complementary oligonucleotides. To this end, provided is a compound capable of hybridizing to at least two exons in a pre-mRNA encoded by a gene, the compound comprising at least two parts, wherein a first part comprises an oligonucleotide having at least eight consecutive nucleotides that are complementary to a first of at least two exons, and wherein a second part comprises an oligonucleotide having at least eight consecutive nucleotides that are complementary to a second exon in the pre-mRNA. The at least two parts are linked in the compound so as to form a single molecule. The linkage may be through any means but is preferably accomplished through a nucleotide linkage. In the latter case, the number of nucleotides that do not contain an overlap between one or the other complementary exon can be zero, but is preferably between 4 to 40 nucleotides. The linking moiety can be any type of moiety capable of linking oligonucleotides. Currently, many different compounds are available that mimic hybridization characteristics of oligonucleotides. Such a compound is also suitable for the invention if such equivalent comprises similar hybridization characteristics in kind, not necessarily in amount. Suitable equivalents were mentioned earlier in this description. One, or preferably more, of the oligonucleotides in the compound are generated by a method for generating an oligonucleotide of the invention. As mentioned, oligonucleotides of the invention do not have to consist of only oligonucleotides that contribute to hybridization to the targeted exon. There may be additional material and/or nucleotides added.

As mentioned, a preferred gene for restructuring mRNA is the DMD gene. The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.6 Mb. Defects may occur in any part of the DMD gene. Skipping of a particular exon or particular exons can very often result in a restructured mRNA that encodes a shorter than normal, but at least partially functional, dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations requires the generation of a large number of different pharmaceuticals; as for different mutations, different exons need to be skipped.

An advantage of a compound capable of inducing skipping of two or more exons, is that more than one exon can be skipped with a single pharmaceutical. This property is practical and very useful in that only a limited number of pharmaceuticals need to be generated for treating many different Duchenne or Becker mutations. Another option now open to the person skilled in the art is to select particularly functional restructured dystrophin proteins and produce compounds capable of generating these preferred dystrophin proteins. Such preferred end results are further referred to as mild phenotype dystrophins. The structure of the normal dystrophin protein can be schematically represented as two end-points having structural function (the beads), which are connected to each other by a long, at least partly flexible, rod. This rod is shortened in many Becker patients.

This led the field to the conclusion that not so much the length of the rod, but the presence of a rod and the composition thereof (with respect to particular hinge regions in the protein), is crucial to the function per se of the dystrophin protein. Though the size of the rod may have an impact on the amount of functionality of the resulting (Becker) protein, there are many notable exceptions. These exceptions will be detailed below. There are especially benign mutations that can have a very short rod. It was noted by the inventors that many more different types of Becker patients should have been detected in the patient population. However, some types of shortened dystrophin proteins, that according to this hypothesis should have a Becker phenotype, are not detected in human population. For some of these "theoretical" Becker forms, this could just be a matter of chance. However, in the invention, it has been found that at least some of these "potential" Becker patients have such a benign phenotype that subjects having these types of mutations do not present themselves to a doctor or are not diagnosed as suffering from Becker's disease. With a compound of the invention, it is possible to restructure DMD pre-mRNA of many different Duchenne and even Becker patients such that a mild phenotype dystrophin is generated after translation of the restructured mRNA.

Thus provided is a particularly preferred compound, wherein the parts of the compounds at least comprise a first part comprising an oligonucleotide or equivalent thereof, complementary to exon 17, and a second part comprising an oligonucleotide or equivalent thereof, complementary to exon 48. The resulting restructured mRNA encodes an in-frame shortened dystrophin protein, lacking all exons from 17 to 48. This shortened dystrophin protein mimics a mild phenotype dystrophin as mentioned above. The compound (referred to as the 17-48 compound) should, according to current databases, be able to deal with as much as 20% of the patients having a DMD mutation currently characterized. Another preferred compound is the 45-55 compound. This compound should, according to the same calculations, be able to deal with 38% of the patients having a DMD mutation thus far characterized.

In yet another embodiment, the compound comprises a 42-55 compound or a 49-59 compound capable of dealing with, respectively, 65% and 18% of the currently characterized DMD patients. Preferred are a 45-49 compound and a 45-51 compound, preferably in the form as disclosed in the experimental part, having the potential to treat, respectively, 4% and 8% of the DMD patients characterized thus far.

Another aspect of the invention is a compound capable of hybridizing to one exon in a pre-mRNA encoded by a gene, the compound comprising at least two parts, wherein a first part comprises an oligonucleotide of which at least a part of the oligonucleotide is complementary to the closed structure and wherein a second part comprises an oligonucleotide of which at least part is complementary to the open structure. The open and closed structures are, of course, determined from a secondary structure of RNA from the exon. A compound having two distinguishable parts complementary to a single exon may comprise an oligonucleotide, or equivalent thereof, or combination thereof, as mentioned herein in the method for generating the oligonucleotide.

A transcription system containing a splicing system can be generated in vitro. The art has suitable systems available. However, the need for mRNA restructuring is, of course, predominantly felt for the manipulation of living cells, preferably, cells in which a desired effect can be achieved through the restructuring of an mRNA. Preferred mRNAs that are restructured are listed hereinabove. Preferably, genes active in muscle cells are used in the invention. Muscle cells (e.g., myotubes) are multinucleated cells in which many, but not all, muscle cell-specific genes are transcribed via long pre-mRNA. Such long pre-mRNAs are preferred for the invention, as restructuring of mRNAs produced from such long mRNAs is particularly efficient. It is thought, though it need not necessarily be so, that the relatively long time needed to generate the full pre-mRNA aids the efficiency of restructuring using a method or means of the invention, as more time is allowed for the process to proceed. The preferred group of genes of which the mRNA is preferably restructured in a method of the invention comprises: COL6A1 causing Bethlem myopathy, MTM1 causing myotubular myopathy, DYSF (dysferlin causing Miyoshi myopathy), and LGMD, LAMA2 (laminin alpha 2) causing Merosin-deficient muscular dystrophy, EMD (emerin) causing Emery-Dreyfuss muscular dystrophy, the DMD gene causing Duchenne muscular dystrophy and Becker muscular dystrophy, and CAPN3 (calpain) causing LGMD2A. Any cell may be used, however, as mentioned, a preferred cell is a cell derived from a DMD patient. Cells can be manipulated in vitro, i.e., outside the subject's body. However, ideally, the cells are provided with a restructuring capacity in vivo. Suitable means for providing cells with an oligonucleotide, equivalent or compound of the invention are present in the art. Improvements in these techniques are anticipated considering the progress that has already thus far been achieved. Such future improvements may, of course, be incorporated to achieve the mentioned effect on restructuring of mRNA using a method of the invention. At present, suitable means for delivering an oligonucleotide, equivalent or compound of the invention to a cell in vivo comprises polyethylenimine (PEI) or synthetic amphiphils (SAINT-18) suitable for nucleic acid transfections. The amphiphils show increased delivery and reduced toxicity, also when used for in vivo delivery. Preferably, compounds mentioned in J. Smisterová, A. Wagenaar, M. C. A. Stuart, E. Polushkin, G. ten Brinke, R. Hulst, J. B. F. N. Engberts, and D. Hoekstra, "Molecular shape of the Cationic Lipid Controls the Structure of the Cationic Lipid/Dioleylphosphatidylethanolamine-DNA Complexes and the Efficiency of Gene Delivery," *J. Biol. Chem.* 2001, 276:47615. The synthetic amphiphils preferably used are based upon the easily synthetically available "long-tailed" pyridinium head group-based materials. Within the large group of amphiphils synthesized, several show a remarkable transfection potential combined with a low toxicity in terms of overall cell survival. The ease of structural modification can be used to allow further modifications and the analysis of their further (in vivo) nucleic acid transfer characteristics and toxicity.

An oligonucleotide, equivalent thereof, or a compound according to the invention may be used for, at least in part, altering recognition of the exon in a pre-mRNA. In this embodiment, the splicing machinery is at least in part prevented from linking the exon boundaries to the mRNA. The oligonucleotide, equivalent or compound of the invention is at least in part capable of altering exon recognition in a pre-mRNA. This use is thus also provided in the invention. The prevention of inclusion of a targeted exon in an mRNA is also provided as a use for, at least in part, stimulating exon skipping in a pre-mRNA. As mentioned above, the targeted exon is not included in the resulting mRNA. However, part of the exon (a neo-exon) may occasionally be retained in the produced mRNA. This sometimes occurs when the targeted exon contains a potential splice acceptor and/or splice donor sequence. In this embodiment, the splicing machinery is redirected to utilize a previously unused (or underused) splice acceptor/donor sequence, thereby creating a new exon (neo-exon). The neo-exon may have one end in common with the paleo-exon, although this does not always have to be the case. Thus, in one aspect, an oligonucleotide, equivalent or compound of the invention is used for altering the efficiency with which a splice donor or splice acceptor is used by a splicing machinery.

In view of the foregoing, further provided is the use of an oligonucleotide, an equivalent thereof, or a compound of the invention for the preparation of a medicament. Further provided is a pharmaceutical preparation comprising an oligonucleotide, equivalent thereof or a compound according to the invention. An oligonucleotide, an equivalent thereof or a compound of the invention can be used for the preparation of a medicament for the treatment of an inherited disease. Similarly provided is a method for altering the efficiency with which an exon in a pre-mRNA is recognized by a splicing machinery, the pre-mRNA being encoded by a gene comprising at least two exons and at least one intron, the method comprising providing a transcription system comprising the splicing machinery and the gene, with an oligonucleotide, equivalent thereof or a compound according to the invention, wherein the oligonucleotide, equivalent thereof or compound is capable of hybridizing to at least one of the exons, and allowing for transcription and splicing to occur in the transcription system. The gene may comprise at least three exons.

An oligonucleotide of the invention may be provided to a cell in the form of an expression vector, wherein the expression vector encodes a transcript comprising the oligonucleotide. The expression vector is preferably introduced into the cell via a gene delivery vehicle. A delivery vehicle may be a viral vector such as an adenoviral vector and, more preferably, an adeno-associated virus vector. Also provided are such expression vectors and delivery vehicles. It is within the skill of the artisan to design suitable transcripts. Preferred for the invention are PolIII-driven transcripts, preferably in the form of a fusion transcript with a U1 or U7 transcript. Such fusions may be generated as described in references 53 and 54.

DETAILED DESCRIPTION

Examples

Example 1

Results

Figure 1:
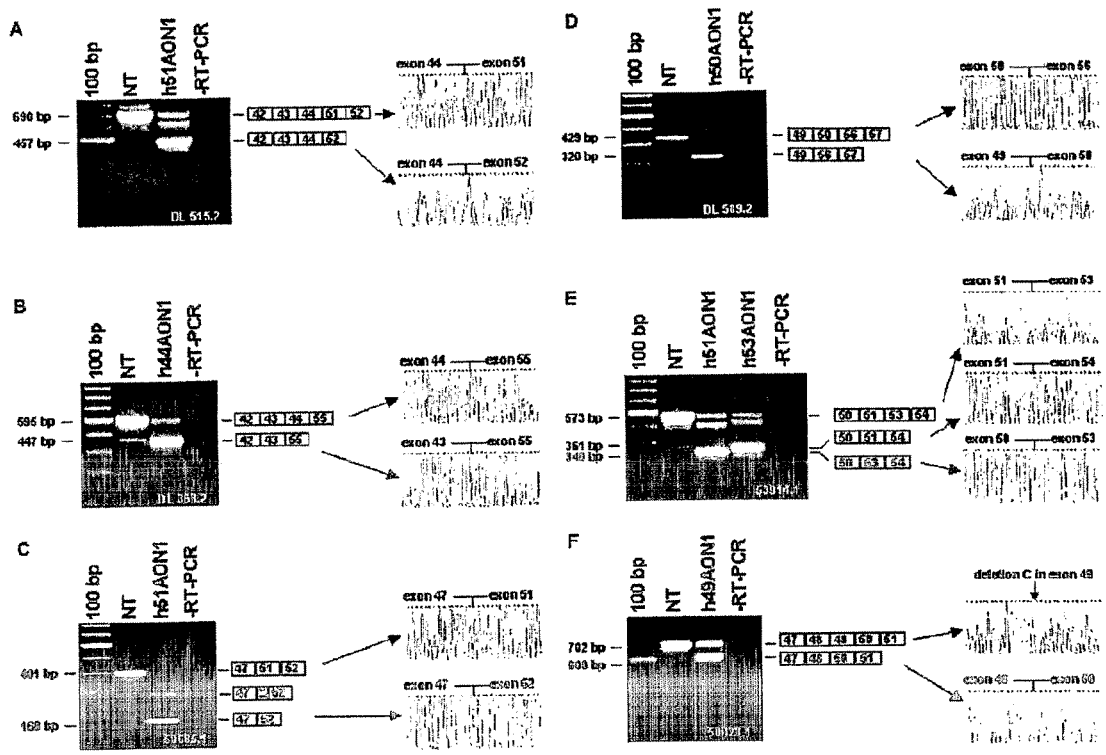
FIG. 1 shows RT-PCR and sequence analysis of dystrophin mRNA fragments of the AON-treated DMD patient myotube cultures, focusing on the regions encompassing the exons targeted for skipping. Shorter novel transcripts were observed when compared to the untransfected myotube cultures (NT). Sequence analysis confirmed the precise skipping of the targeted exons. An alternatively spliced product, detected for patient 50685.1 (Panel C) was sequenced and found to be derived from activation of a cryptic splice site in exon 51. Shorter fragments, detected in untransfected myotube cultures from DL 363.2 (Panel B), DL 589.2 (Panel D) and 53914.1 (Panel E), were sequenced and found to be the result of the spontaneous skipping of exons 44, 50 and 53, respectively. Note that in some analyses, additional fragments, slightly shorter than the wild-type products, were present. This was due to heteroduplex formation. 100 bp: size marker, —RT-PCR: negative control.

This study includes six DMD patients affected by different mutations (Table 1). Patient DL 515.2 carries an exon 45-50 deletion; hence exon 51 skipping would be frame correcting. Patient DL 363.2 has a deletion of exon 45-54; the reading frame for this patient would be corrected by an exon 44 skip. For patient 50685.1, who is affected by an exon 48-50 deletion, reading frame correction requires an exon 51 skip. Patient DL 589.2 has an exon 51-55 deletion; the reading frame would be corrected by an exon 50 skip. Patient 53914.1 carries a single-exon 52 deletion. Notably, in this case, both the skipping of exon 51 or exon 53 would be frame correcting. Finally, patient 50423.1 has a deletion of a single base pair in exon 49, at position 7389 on cDNA level, resulting in a frame-shift and a premature stop codon in exon 49. Since exon 49 is an in-frame exon, skipping of this exon would correct the reading frame for this patient.

We have previously identified AONs with which the skipping of the mentioned target exons 44, 49, 50, 51 and 53 can be induced at concentrations of 1 µM (23). In subsequent dose-response experiments, however, we have obtained substantial skipping efficiencies with lower concentrations of 500 nM or 200 nM, and even 100 nM for most AONs (data not shown). This had the extra advantageous effect of lower doses of PEI required for transfection, which significantly reduced the levels of cytotoxicity as found in our earlier transfection experiments. Myotube cultures from the six DMD patients were transfected with the relevant AONs. On average, 70% to 90% of cells showed specific nuclear uptake of fluorescent AONs. RNA was isolated 24 hours post-transfection and analyzed by RT-PCR (FIG. 1). In all patients, the targeted exons were skipped at high efficiencies, and precisely at the exon boundaries, as confirmed by sequence analysis of the novel shorter transcripts (FIG. 1). For patient 50685.1, an additional transcript fragment was found (FIG. 1, Panel C). Sequence analysis showed that this was generated by the activation of a cryptic splice site in exon 51. This was previously also observed in human control cells treated with the same AON (23). Remarkably, low levels of spontaneous exon skipping were observed in untreated cells derived from patients DL 363.2 (exon 44 skip), DL 589.2 (exon 50 skip), and 53914.1 (exon 53 skip). RT-PCR analysis on several larger areas of the DMD gene transcript did not reveal additional, unexpected, aberrant splicing patterns induced by the AON-treatment.

Figure 2:
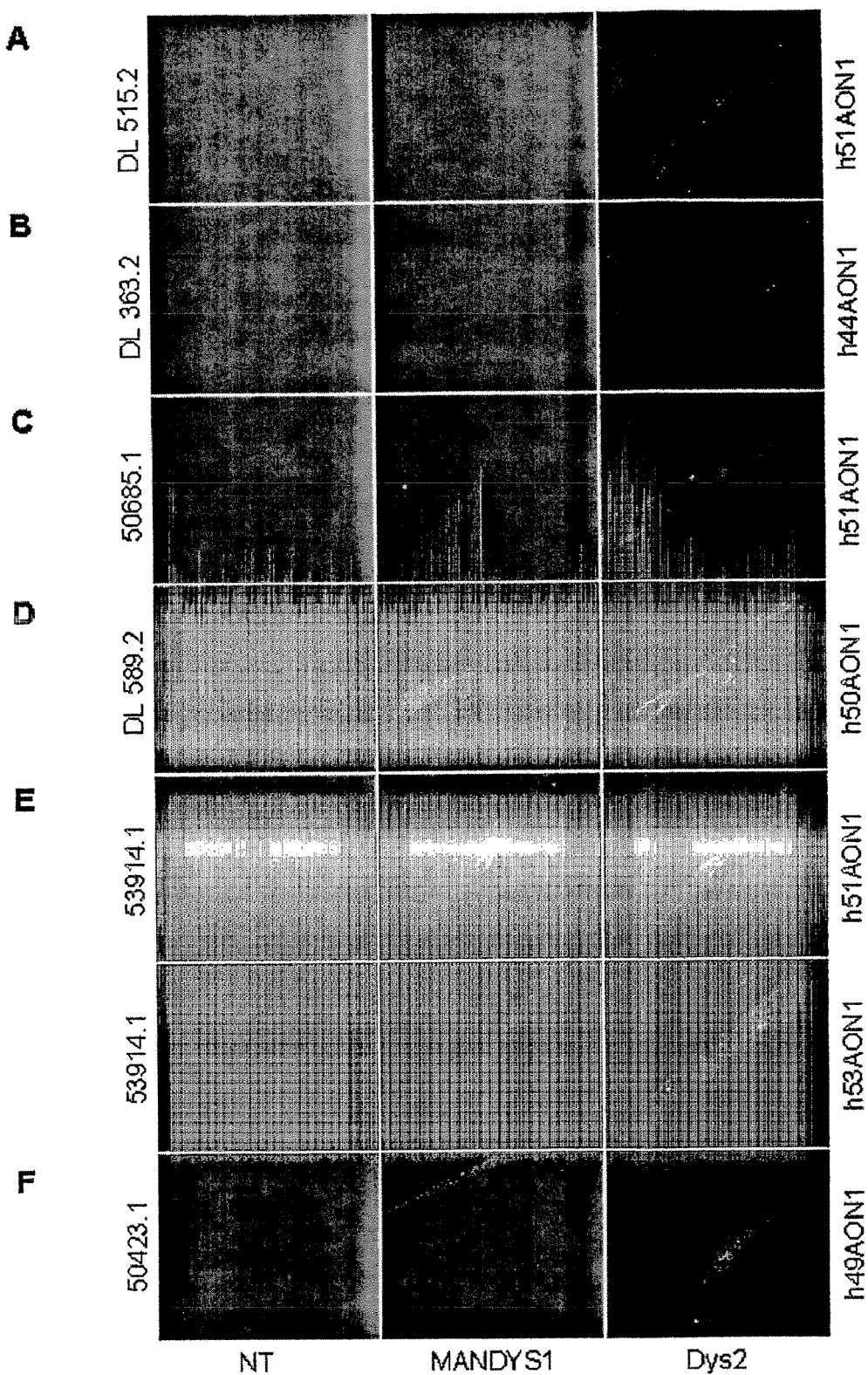
FIG. 2 illustrates immuno-histochemical analysis of the AON-treated myotube cultures from the six different DMD patients. Cells were stained for myosin to identify fully differentiated myotubes (not shown). Monoclonal antibodies MANDYS1 (middle panel) and Dys2 (right panel) were used to detect dystrophin one to four days post-transfection. No dystrophin signals could be detected in untreated cells stained with MANDYS1 (left panel) nor Dys2 (not shown), whereas clear, mainly cytoplasmatic dystrophin signals could be detected for each patient upon the induced exon skipping. In patients DL 363.2 (row B), DL 589.2 (row D) and 53914.1 (row E), dystrophin membrane signals could be observed. Note that membrane signals were more often found for Dys2, which recognizes the full-length dystrophin. MANDYS1 recognizes an internal part of dystrophin and is more prone to generate cytoplasmatic signals, since it also detects dystrophin in the first stages of synthesis. Magnification 63×.
Figure 3:
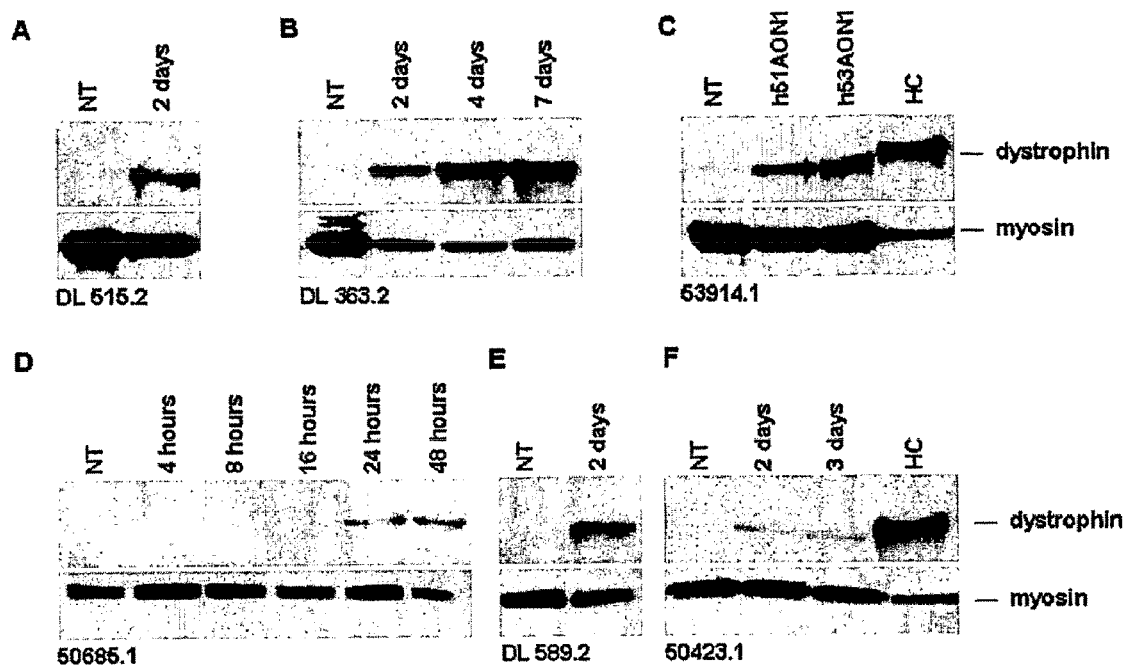
FIG. 3 is Western blot analysis of the AON-treated myotube cultures. Monoclonal antibody DY4 was used to detect dystrophin. Protein extracts isolated from human control myotube cultures (HC) were used as a positive control (Panels C and F). To avoid over-exposure, this sample was 1 to 10 diluted. To demonstrate equal loading of protein samples, blots were additionally stained with an antibody against myosin. No, or, as a result of spontaneous exon skipping, very low (Panels B and C) levels of dystrophin were detected in non-transfected myotube cultures (NT). Clear dystrophin signals were observed in AON-treated myotube cultures for each of the patients. For 50685.1 and DL 363.2, a time-course experiment was performed. Dystrophin could be detected 16 hours post-transfection and was found at increasing levels at 24 hours and 48 hours post-transfection for 50685.1 (Panel D). For DL 363.2, dystrophin could be detected in increasing levels up to seven days post-transfection (Panel B). For patients DL 515.2 (Panel A), DL 363.2 (Panel B) and DL 589.2 (Panel E), the detected dystrophin was significantly shorter than the control dystrophin. This is due to the size of the deletions in these patients.

The resulting in-frame transcripts should restore dystrophin synthesis. Indeed, immuno-histochemical analysis of transfected myotube cultures detected dystrophin in the majority of myotubes for each patient (FIG. 2). The therapeutic efficiency was determined by double staining, using antibodies against myosin, to identify sufficiently differentiated myotubes and dystrophin. On average, 75% to 80% of myosin-positive myotubes showed dystrophin expression. We observed clear membrane-bound dystrophin for patients DL 363.2, DL 589.2 and 53914.1 two days post-transfection (FIG. 2, rows B, D, and E). The presence of dystrophin was confirmed for each patient by Western blot analysis (FIG. 3). For patients 50685.1 and DL 363.2, we performed time course experiments, which indicated that dystrophin can be detected as soon as 16 hours post-transfection (FIG. 3, Panel D) and at increasing levels up to seven days post-transfection (FIG. 3, Panel B). The dystrophin proteins from patients DL515.2, DL 363.2 and DL 589.2 are significantly shorter than the human control, which is due to the size of the deletion.

Figure 4:
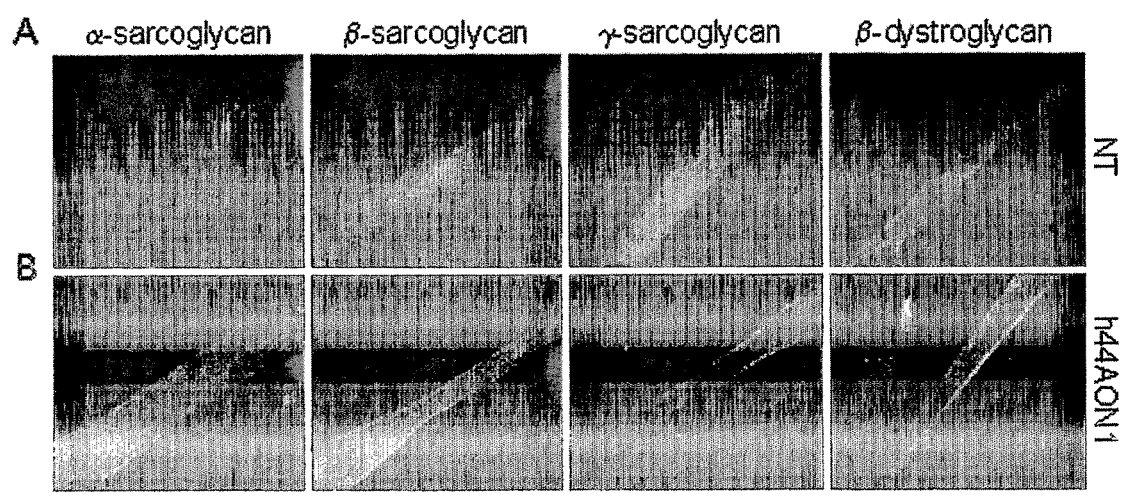
FIG. 4 shows immuno-histochemical analysis of four DGC proteins from treated myotube cultures from patient DL 363.2. Cells were stained for myosin to identify sufficiently differentiated myotubes (not shown). Monoclonal antibodies NCL-a-SARC, NCL-b-SARC, NCL-g-SARC and NCL-b-DG were used to detect α-sarcoglycan, β-sarcoglycan, γ-sarcoglycan and β-dystroglycan, respectively. These proteins were detected in reduced percentages (~40%) in untreated myotubes, and were mainly located in the cytoplasm (row A). Following AON treatment, however, α-sarcoglycan was detected in 70%, β-sarcoglycan was detected in 90%, γ-sarcoglycan was detected in 90% and β-dystroglycan was detected in 80% of the myotubes, and the proteins were mostly membrane-bound (row B). Magnification 63×.

For one patient, DL 363.2, we also assessed whether the induction of the dystrophin synthesis resulted in the restoration of the DGC (FIG. 4). Prior to AON treatment, we found reduced, mainly cytoplasmatic alpha, beta, gamma sarcoglycan and beta-dystroglycan signals (30%, 30%, 40% and 80%, respectively) (FIG. 4, row A). Following AON transfection, increased levels of mainly membrane-bound alpha-, beta- and gamma-sarcoglycans and beta-dystroglycan were detected in 70%, 90%, 90% and 80% of the treated myotube cultures, respectively (FIG. 4, row B).

Discussion

The reading frame correction strategy for DMD patients is aimed at antisense-induced, targeted exon skipping. This would convert a severe DMD phenotype into a mostly milder BMD phenotype. We determined the broad applicability in six patients, carrying five different deletions and a point mutation in an exon 49 (Table 1). Following AON treatment, we show for each patient the precise skipping of the targeted exon on the RNA level, and a dystrophin protein in 75% to 80% of the treated myotubes. In particular, we here report, for the first time, the application of a single AON treatment (i.e., the induced skipping of exon 51) to correct the reading frame for several different deletions.

Interestingly, the levels of exon skipping observed in the DMD patient cells are significantly higher than those previously obtained in human control cells (23). Typically, the novel skip transcript is the major product. This can be explained by the action of the nonsense-mediated decay (NMD) process (25, 32). In control cells, the skip of an out-of-frame exon results in an out-of-frame transcript, which will be susceptible to NMD. In patient cells, the skip of a target exon results in an in-frame transcript that would be resistant to NMD and thus more stable than the out-of-frame transcript originally present.

For three of the patients (DL 363.2, DL 589.2 and 53914.1), we detected low levels of spontaneous skipping of exons 44, 50 and 53 in untreated cells. This phenomenon has previously also been described for so-called revertant muscle fibers (33-35). These dystrophin-positive fibers are present in low amounts (2% to 10%) in DMD muscles and are considered to be the result of secondary somatic mutations and/or alternative splicing that restore the reading frame. The existence of revertant fibers has been suggested to correlate with the severity of the disease (36, 37).

Restoration of the dystrophin synthesis could be detected as soon as 16 hours post-transfection. At two days post-transfection, dystrophin was detected at the membrane, indicating that these novel BMD-like proteins are likely in part functional. Furthermore, we show that restoration of the dystrophin synthesis appears to re-establish the formation of the dystrophin-glycoprotein complex.

In patients DL 363.2 and DL 589.2, the targeted exon skipping enlarged the deletions to span exons 44-54 and 50-55, respectively. So far, these deletions have not been reported in DMD or BMD patients. This means that they either do not exist or generate a very mild phenotype not diagnosed as BMD. Considering both the large variety of BMD mutations and the markedly lower incidence of BMD observed, we consider the last explanation more plausible than the first. The out-of-frame deletions from patients DL 515.1, 50685.1 and 50423.1 were converted into in-frame deletions as observed in BMD patients carrying deletions of exon 45-51, exon 48-51 and exon 49 (30, 38-40); noteworthy, the exon 48-51 deletion has even been described in an asymptomatic person (40). On the other hand, however, there are also DMD patients carrying such deletions (38, 41-43). Since most of these theoretical in-frame deletions have been detected on the DNA level only, we hypothesize that the dystrophin deficiency in these DMD patients may be caused by additional aberrant splicing patterns on the RNA level, resulting in an out-of-frame transcript.

It is feasible to correct over 75% of the mutations reported in the Leiden DMD-mutation database (30). Our results indicate that antisense-induced reading frame correction will be a promising therapeutic approach for many DMD patients carrying different deletions and point mutations. Towards the establishment of clinical trials, we are currently investigating and optimizing delivery methods in muscle tissue of mice in vivo.

Material and Methods

AONs and Primers

The AONs applied (Table 1) were previously described (23). They contain a 5' fluorescein group (6-FAM), a full-length phosphorothioate backbone and 2'-O-methyl modified ribose molecules (Eurogentec, BE). To avoid interference with the fluorescent signals of the secondary antibodies, unlabelled AONs were used for immuno-histochemical analyses. Primers for RT-PCR analysis (sequences available upon request) were synthesized by Eurogentec (BE) or by Isogen Bioscience BV (NL).

Myogenic Cell Cultures and AON Transfections

Primary human myoblasts from patients DL 515.2 (deletion exon 45-50), DL 363.2 (deletion exon 45-54), 50685.1 (deletion exon 48-50), DL 589.2 (deletion exon 51-55) and 53914.1 (deletion exon 52) were isolated from a muscle biopsy and cultured as described (44). Cultures were seeded in collagen pre-coated flasks and plates (Vitrogen 100, Cohesion). Myotubes were obtained from confluent myoblast cultures, following 7 to 14 days of serum deprivation. They were subsequently transfected using polyethylenimine (PEI) for three hours in low-serum medium, according to the manufacturer's instructions (ExGen500; MBI Fermentas), and with 3.5 μl PEI applied per μg of transfected AON. For RT-PCR analysis, concentrations of 500 nM AON were used. At this concentration, the highest skipping levels can be obtained, albeit with moderate levels of cell death. Because more viable myotubes are required for immunohistochemical and western blot analysis, concentrations of 200 nM were applied.

For patient 50423.1, who carries a point mutation in exon 49, only fibroblasts were available. Following infection (MOI 50-100) with an adenoviral vector containing the MyoD gene (Ad50MyoD), the fibroblasts were forced into myogenesis according to protocols described previously (45-47). Two hours post-infection, the medium was replaced by low-serum medium, and cells were incubated for eight to ten days until myotubes were formed. Transfection conditions were identical to those described above.

RNA Isolation and RT-PCR Analysis

At 24 hours post-transfection, total RNA was isolated from the myotube cultures (RNA-Bee RNA isolation solvent, Campro Scientific, NL). 300 ng of total RNA was used for RT-PCR analysis using C.therm polymerase (Roche Diagnostics, NL) in a 20 μl reaction at 60° C. for 30 minutes, primed with different DMD gene-specific reverse primers (Table 1). Primary PCRs were performed by 20 cycles of 94° C. (40 seconds), 60° C. (40 seconds) and 72° C. (60 seconds). One μl of these reactions was then reamplified in nested PCRs by 32 cycles of 94° C. (40 seconds), 60° C. (40 seconds) and 72° C. (60 seconds). PCR products were analyzed on 1.5% or 2% agarose gels. Noteworthy, no evidence for a significant preference for the amplification of shorter fragments was obtained in PCR analyses on a defined series of mixtures of known quantities of the normal and shorter transcript fragments (data not shown).

Sequence Analysis

RT-PCR products were isolated from agarose gels using the QIAQUICK® Gel Extraction Kit (Qiagen). Direct DNA sequencing was carried out by the Leiden Genome Technology Center (LGTC) using the BigDye Terminator Cycle Sequencing Ready Reaction kit (PE Applied Biosystems) and analyzed on an ABI 3700 Sequencer (PE Applied Biosystems).

Protein Isolation and Western Blot Analysis

Protein extracts were isolated from treated myotube cultures (25 cm² flasks), using 150 μl of treatment buffer (75 mM Tris-HCl pH 6.8, 15% SDS, 5% b-mercaptoethanol, 2% glycerol, 0.001% bromophenol blue), at two to four days post-transfection, depending on the survival rate of the myotubes. For the time course experiments, protein extracts were isolated 4 hours, 8 hours, 16 hours, 24 hours and 48 hours post-transfection (for patient 50685.1) or at 2 days, 4 days and 7 days post-transfection (for patient DL 363.2).

Polyacrylamide gel electrophoresis and Western blotting were performed as described by Anderson et al., with some minor adjustments (48). Briefly, samples (75 μl) were run overnight at 4° C. on a 4% to 7% polyacrylamide gradient gel. Gels were blotted to nitrocellulose for five to six hours at 4° C. Blots were blocked for one hour with 5% non-fat dried milk in TBST buffer (10 mM Tris-HCl, 0.15 M NaCl, 0.5% Tween 20, pH 8), followed by an overnight incubation with NCL-DYS2 (which recognizes dystrophin) diluted 1:50. HRP-conjugated anti-mouse (Santa Cruz) diluted 1:10,000 was used as a secondary antibody. Immuno-reactive bands were visualized using Lumi-Lightplus Western Blotting Substrate and scanned with a Lumi-Imager (Roche Diagnostics, NL).

Immunohistochemical Analysis

Treated myotube cultures were fixed in −20° C. methanol at one to four days post-transfection, depending of the survival rate of the myotubes. Prior to reaction with the different antibodies, the cells were incubated for one hour in a blocking solution containing 5% horse serum (Gibco BRL) and 0.05% Tween-20 (Sigma) in PBS (Gibco BRL). All antibodies used were diluted in this blocking solution. The following antibodies were applied: desmin polyclonal antibody (ICN Biomedicals) diluted 1:100, myosin monoclonal antibody diluted 1:100 (MF20; Developmental Studies Hybridoma Bank, University of Iowa), myosin polyclonal antibody L53 diluted 1:100 (a gift from Dr. M. van den Hoff, AMC, NL), MANDYS1 (a gift from Dr. G. Morris, North East Wales Institute, UK) diluted 1:10 and NCL-DYS2 (Novacastra Laboratories Ltd) diluted 1:10 to detect dystrophin, NCL-a-SARC (Novacastra Laboratories Ltd) diluted 1:75, NCL-b-SARC (Novacastra Laboratories Ltd) diluted 1:50, NCL-g-SARC (Novacastra Laboratories Ltd) diluted 1:50 and NCL-b-DG (Novacastra Laboratories Ltd) diluted 1:50 to detect α-sarcoglycan, β-sarcoglycan, γ-sarcoglycan and β-dystroglycan, respectively. After one hour incubation, slides were rinsed and incubated for one hour with the secondary antibodies Alexa Fluor 594 goat anti-rabbit conjugate diluted 1:1000 or Alexa Fluor 488 goat anti-mouse conjugate diluted 1:250 (Molecular Probes Inc). The slides were analyzed using a Leica confocal microscope equipped with epifluorescence optics. Digital images were captured using a CCD camera (Photometrics).

Example 2

Materials and methods

AONs and Primers

A series of AONs (two per exon, see Table 2) was designed to bind to exon-internal target sequences showing a relatively high purine-content and, preferably, an open secondary pre-mRNA structure (at 37° C.), as predicted by the RNA mfold version 3.1 server [22]. The AONs varied in length between 15 and 24 bp, with G/C contents between 26 and 67%. They were synthesized with the following chemical modifications: a 5'-fluorescein group (6-FAM), a full-length phosphorothioate backbone and 2'-O-methyl-modified ribose molecules (Eurogentec, BE). The primers used for reverse transcription-polymerase chain reaction (RT-PCR) analysis (Table 3) were synthesized by Eurogentec (BE) or by Isogen Bioscience BV (NL).

In Vitro Experiments

Primary human myoblasts were isolated from a muscle biopsy from a non-affected individual (KM108) by enzymatic dissociation. Briefly, the tissue was homogenized in a solution containing 5 mg/ml collagenase type VIII (Sigma), 5 mg/ml bovine albumin fraction V (Sigma), 1% trypsin (Gibco BRL) in PBS (Gibco BRL). Following serial incubation steps of 15 minutes at 37° C., suspensions containing the dissociated cells were added to, and pooled in, an equal volume of proliferation medium (Nut.Mix F-10 (HAM) with GlutaMax-1, Gibco BRL) supplemented with 20% fetal bovine serum (Gibco BRL) and 1% penicillin/streptomycin solution (Gibco BRL). After centrifugation, the cells were plated and further cultured in proliferation medium, using flasks that were pre-coated with purified bovine dermal collagen (Vitrogen 100; Cohesion).

The myogenic cell content of the culture, as determined by the percentage of desmin-positive cells in an immunohistochemical assay, was improved to 58% by repetitive pre-plating [23]. Myotubes were obtained from confluent myoblast cultures following 7 to 14 days of incubation in low-serum medium (DMEM (Gibco BRL), supplemented with 2% GlutaMax-1, 1% glucose, 2% fetal bovine serum and 1% penicillinlstreptomycin solution). For transfection of the myotube cultures, we used polyethylenimine (PEI; ExGen 500) according to the manufacturer's instructions (MBI Fermentas). The cultures were transfected for three hours in low-serum medium with 1 mM of each AON linked to PEI at a ratio-equivalent of 3.5.

RNA isolation and RT-PCR analysis at 24 hours post-transfection, total RNA was isolated from the myotube cultures using RNAzol B according to the manufacturer's instructions (Campro Scientific, NL). One microgram of RNA was then used for RT-PCR analysis using C. therm. polymerase (Roche Diagnostics) in a 20 µl reaction at 60° C. for 30 minutes, primed with different DMD gene-specific reverse (RT) primers (Table 3). Primary PCRs were carried out with outer primer sets (see Table 3), for 20 cycles of 94° C. (40 seconds), 60° C. (40 seconds), and 72° C. (90 seconds). One microliter of this reaction was then reamplified in nested PCRs using the appropriate primer combinations (Table 3) for 32 cycles of 94° C. (40 seconds), 60° C. (40 seconds), and 72° C. (60 seconds). PCR products were analyzed on 1.5 or 2% agarose gels.

Sequence analysis RT-PCR products were isolated from agarose gels using the QIAQUICK® Gel Extraction kit (Qiagen). Direct DNA sequencing was carried out by the Leiden Genome Technology Center (LGTC) using the BIG-DYE® Terminator Cycle Sequencing Ready Reaction kit (PE Applied Biosystems), and analyzed on an ABI 3700 Sequencer (PE Applied Biosystems).

Results

In Vitro Exon Skipping

Figure 5:
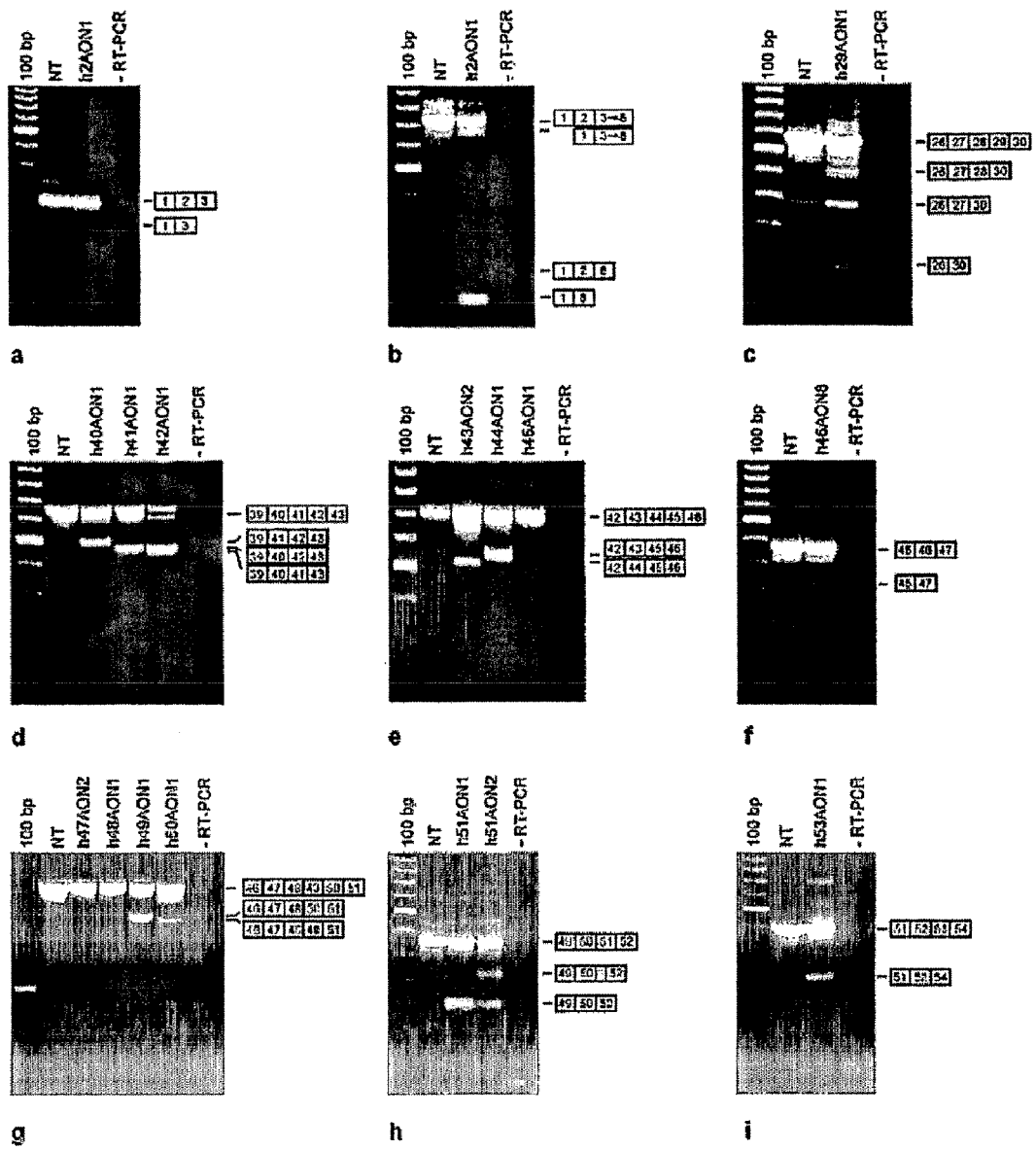
FIG. 5 is RT-PCR analysis of human dystrophin mRNA in the regions encompassing the exons targeted for skipping. Shorter novel transcript fragments were observed following transfection with the different AONs when compared to non-transfected myotube cultures (NT). Sequence analysis (not shown) confirmed the skipping of the targeted exons, as indicated by the labels adjacent to the images. Alternatively spliced products, detected in the regions around exon 2 (b), exon 29 (c), and exon 51 (h), were sequenced and found to be derived from either co-skipping of adjacent exons or usage of a cryptic splice site. No specific (RT-) PCR products were obtained. In some analyses, additional fragments, lightly shorter than the wild-type products, were present. This was due to heteroduplex formation.

AONs were empirically analyzed for the induction of exon skipping following transfection into human control myotube cultures, using the cationic polymer polyethylenimine (PEI). As determined by the nuclear uptake of the fluorescent AONs, average transfection efficiencies of 60-80% were obtained. At 24 hours post-transfection, transcripts were analyzed by RT-PCR using different primer combinations encompassing the targeted exons (Table 3). Of the 30 AONs tested, a total of 21 (70%) reproducibly generated shorter transcript fragments with sizes corresponding to the specific skipping of the targeted exons (FIG. 5 and Table 2). In fact, as confirmed by sequence analysis of the shorter transcripts (data not shown), we could induce the specific skipping of 13 out of the 15 exons targeted (five out of the seven in-frame exons, and eight out of the eight out-of-frame exons). No skipping of exons 47 and 48 was detected (FIG. 5, Panels e and g).

In the specific transcript regions that were screened in these experiments, we observed in the non-transfected control myotubes, alternative splicing patterns around exons 2 and 29 (FIG. 5, Panels b and c). The alternative products were sequenced and found to be due to the skipping of exons 2-7 (in-frame), exons 3-7 (out-of-frame), exons 28-29 (in-frame), and exons 27-29 (in-frame). This genuinely occurring exon skipping was also detected previously in human skeletal muscle [24, 25]. Remarkably, the level of the alternative splicing was significantly enhanced by the AON treatment of the transfected myotube cultures. Also noteworthy is the observation that h2AON1 not only induced exon 2 skipping in the normal transcript, but also in one of the alternative transcripts consisting of exons 1 and 2 spliced to exon 8 (FIG. 5, Panel b).

The majority of AONs induced the precise skipping of the targeted exons, using the original splice sites of the adjacent exons. However, in response to h51AON2, an in-frame cryptic splice site was used in exon 51 (FIG. 5, Panel h). The level of this alternatively spliced product was variable in serial transfection experiments. Finally, in some of the transfection experiments, additional aberrant splicing fragments were detected due to the co-skipping of adjacent exons. Their incidence, however, was inconsistent, and at very low levels.

References to Example 2 (numbering in this part refers strictly to numbering used in Example 2)

[1] Hoffman E. P., R. H. Brown Jr., and L. M. Kunkel. Dystrophin: the protein product of the Duchenne muscular dystrophy locus. Cell 1987, 51:919-928.

[2] Monaco A. P., C. J. Bertelson, S. Liechti-Gallati, H. Moser, and L. M. Kunkel. An explanation for the phenotypic differences between patients bearing partial deletions of the DMD locus. Genomics 1988, 2:90-95.

[3] Koenig M., A. H. Beggs, and M. Moyer, et al. The molecular basis for Duchenne versus Becker muscular dystrophy: correlation of severity with type of deletion. Am. J. Hum. Genet. 1989, 45:498-506.

[4] Zubrzycka-Gaarn E. E., D. E. Bulman, and G. Karpati, et al. The Duchenne muscular dystrophy gene product is localized in sarcolemma of human skeletal muscle. Nature 1988, 333:466-469.

[5] Yoshida M. and E. Ozawa. Glycoprotein complex anchoring dystrophin to sarcolemma. J. Biochem. (Tokyo) 1990, 108:748-752.

[6] Ervasti J. M. and K. P. Campbell. Membrane organization of the dystrophin-glycoprotein complex. Cell 1991, 66:1121-1131.

[7] Koenig M., A. P. Monaco and L. M. Kunkel. The complete sequence of dystrophin predicts a rod-shaped cytoskeletal protein. Cell 1988, 53:219-226.

[8] van Deutekom J. C., S. S. Floyd and D. K. Booth, et al. Implications of maturation for viral gene delivery to skeletal muscle. Neuromuscul. Disord. 1998, 8:135-148.

[9] Mayeda A., Y. Hayase, H. Inoue, E. Ohtsuka and Y. Ohshima. Surveying cis-acting sequences of pre-mRNA by adding antisense 20-O-methyl oligoribonucleotides to a splicing reaction. J. Biochem. (Tokyo) 1990, 108:399-405.

[10] Galderisi U., A. Cascino and A. Giordano. Antisense oligonucleotides as therapeutic agents. J. Cell. Physiol. 1999, 181:251-257.

[11] Baker B. F. and B. P. Monia. Novel mechanisms for antisense-mediated regulation of gene expression. Biochim. Biophys. Acta 1999, 1489:3-18.

[12] Kole R. and P. Sazani. Antisense effects in the cell nucleus: modification of splicing. Curr. Opin. Mol. Ther. 2001, 3:229-234.

[13] Sicinski P., Y. Geng, A. S. Ryder-Cook, E. A. Barnard, M. G. Darlison and P. J. Barnard. The molecular basis of muscular dystrophy in the mdx mouse: a point mutation. Science 1989, 244:1578-1580.

[14] Dunckley M. G., M. Manoharan, P. Villiet, I. C. Eperon and G. Dickson. Modification of splicing in the dystrophin gene in cultured Mdx muscle cells by antisense oligoribonucleotides. Hum. Mol. Genet. 1998, 7:1083-1090.

[15] Mann C. J., K. Honeyman and A. J. Cheng, et al. Antisense-induced exon skipping and synthesis of dystrophin in the mdx mouse. Proc. Natl. Acad. Sci. U.S.A. 2001, 98:42-47.

[16] Wilton S. D., F. Lloyd and K. Carville, et al. Specific removal of the nonsense mutation from the mdx dystrophin mRNA using anti-sense oligonucleotides. Neuromuscul. Disord. 1999, 9:330-338.

[17] Takeshima Y., H. Wada, M. Yagi, et al. Oligonucleotides against a splicing enhancer sequence led to dystrophin production in muscle cells from a Duchenne muscular dystrophy patient. Brain Dev. 2001, 23:788-790.

[18] Pramono Z. A., Y. Takeshima, H. Alimsardjono, A. Ishii, S. Takeda and M. Matsuo. Induction of exon skipping of the dystrophin transcript in lymphoblastoid cells by transfecting an antisense oligodeoxynucleotide complementary to an exon recognition sequence. *Biochem. Biophys. Res. Commun.* 1996, 226:445-449.

[19] Watakabe A., K. Tanaka and Y. Shimura. The role of exon sequences in splice site selection. *Genes Dev.* 1993, 7:407-418.

[20] Tanaka K., A. Watakabe and Y. Shimura. Polypurine sequences within a downstream exon function as a splicing enhancer. *Mol. Cell. Biol.* 1994, 14:1347-1354.

[21] van Deutekom J. C., M. Bremmer-Bout, A. A. Janson, et al. Antisense-induced exon skipping restores dystrophin expression in DMD patient-derived muscle cells. *Hum. Mol. Genet.* 2001, 10:1547-1554.

[22] Mathews D. H., J. Sabina, M. Zuker and D. H. Turner. Expanded sequence dependence of thermodynamic parameters improves prediction of RNA secondary structure. *J. Mol. Biol.* 1999, 288:911-940.

[23] Richler C. and D. Yaffe. The in vitro cultivation and differentiation capacities of myogenic cell lines. *Dev. Biol.* 1970, 23:1-22.

[24] Surono A., Y. Takeshima, T. Wibawa, Z. A. Pramono and M. Matsuo. Six novel transcripts that remove a huge intron ranging from 250 to 800 kb are produced by alternative splicing of the 50 region of the dystrophin gene in human skeletal muscle. *Biochem. Biophys. Res. Commun.* 1997, 239:895-899.

[25] Shiga N., Y. Takeshima, H. Sakamoto, et al. Disruption of the splicing enhancer sequence within exon 27 of the dystrophin gene by a nonsense mutation induces partial skipping of the exon and is responsible for Becker muscular dystrophy. *J. Clin. Invest.* 1997, 100:2204-2210.

[26] Wells D. J., K. E. Wells, E. A. Asante, et al. Expression of human full-length and minidystrophin in transgenic mdx mice: implications for gene therapy of Duchenne muscular dystrophy. *Hum. Mol. Genet.* 1995, 4:1245-1250.

[27] Sironi M., U. Pozzoli, R. Cagliani, G. P. Comi, A. Bardoni and N. Bresolin. Analysis of splicing parameters in the dystrophin gene: relevance for physiological and pathogenetic splicing mechanisms. *Hum. Genet.* 2001, 109:73-84.

A. Aartsma-Rus et al., *Neuromuscular Disorders* 12 (2002) S71-S77.

Example 3

Results

Double-Exon Skipping in Two DMD Patients

This study includes two DMD patients affected by different frame-disrupting mutations in the DMD gene that require the skip of two exons for correction of the reading frame (Table 5). Patient DL 90.3 carries a nonsense mutation in exon 43. Considering that this single exon is out-of-frame, the skipping of exon 43 would remove the nonsense mutation but not restore the reading frame.

Figure 6:
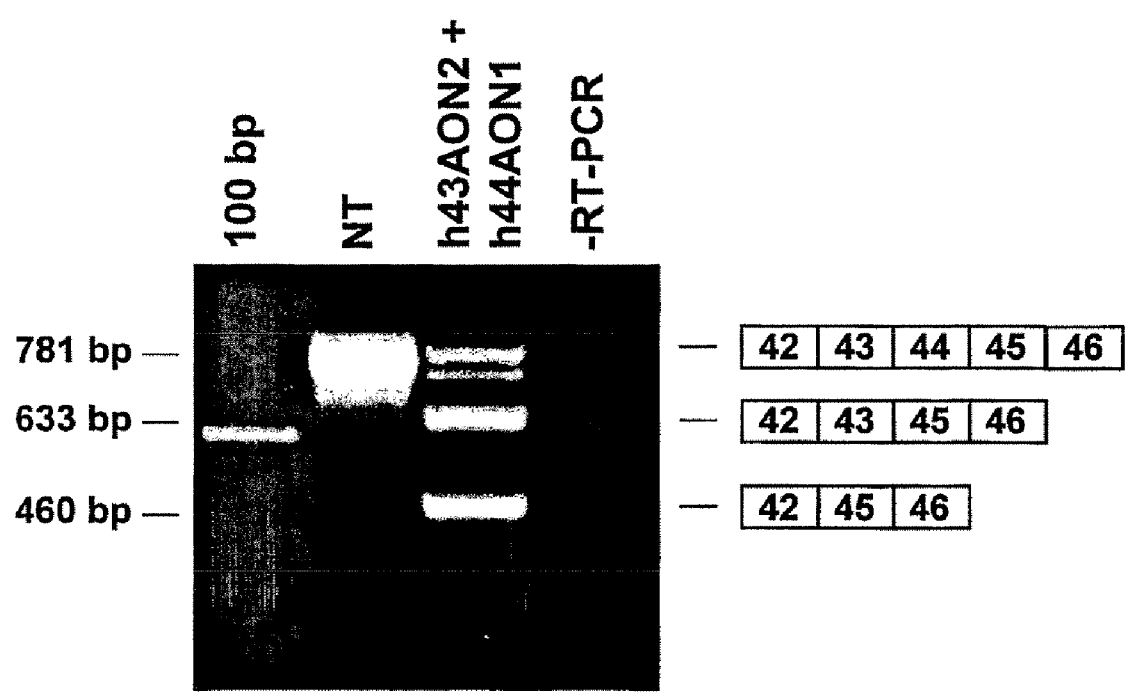
FIG. 6 illustrates double-exon skipping in DMD patient DL90.3 carrying a nonsense mutation in the out-of-frame exon 43. RT-PCR analysis of dystrophin mRNA fragments of AON-treated myotubes from this patient showed a shorter, novel transcript not present in untransfected myotubes (NT). Sequence analysis confirmed the precise skipping of the targeted exons 43 and 44. Besides this double-skip, we also detected a single-exon 44 skip. Note that the additional fragment, slightly shorter than the wild-type product, is due to heteroduplex formation. 100 bp: size marker, -RT-PCR: negative control.
Figure 7:
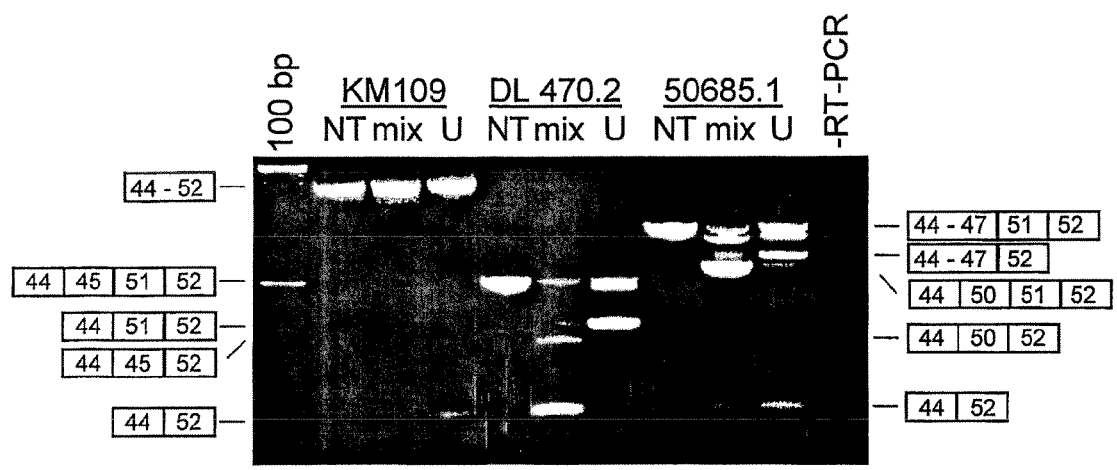
FIG. 7 illustrates double- and multi-exon skipping in human control myotubes (KM 109), DMD patient DL 470.2, carrying a deletion of exons 46 to 50, and DMD patient 50685.1, carrying a deletion of exons 48 to 50. Panel A is RT-PCR analysis of dystrophin mRNA fragments in the myotube cultures treated with either a mixture of h45AON5 and h51AON2 (mix) or with a U-linked combination of AONs (U: h45AON5 linked to h51AON2 by ten uracil nucleotides). In all samples treated with either the mix of AONs or the U-linker AON, a shorter transcript fragment was detected that contained exon 44 spliced to exon 52, and that was not present in untreated myotubes (NT). This novel, in-frame transcript arose from double-exon skipping in patient DL 470.2 (the targeted exons 45 and 51 are directly flanking the deletion), but from multi-exon skipping in both the human control and patient 50685.1. In the treated patient myotube cultures, additional shorter fragments were observed due to single-exon 45 and single-exon 51 skipping. Note that in some lanes, other fragments, slightly shorter than the wild-type products, were present. This was due to heteroduplex formation. 100 bp: size marker, -RT-PCR: negative control. Panel B shows that all fragments were quantified using the DNA 7500 LABCHIP® and the BIOANALYZER™ (Agilent). The percentage of double- or multi-exon 45 to 51 skipping was determined by the ratio of this fragment to the total of transcript fragments. The U-combined AON seems less efficient in DL 470.2, but more efficient in KM 109 and 50685.1, when compared to the mixture of AONs.
Figure 7:
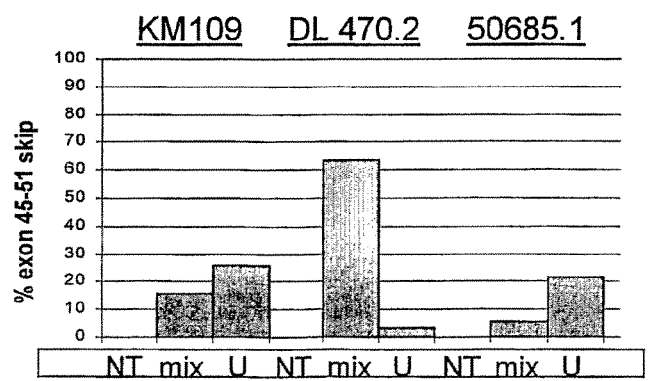

Since the combination with exon 44 is in-frame, in this patient, we aimed at double-exon skipping, targeting both these exons. Patient DL 470.2 is affected by a deletion of exons 46 to 50. Frame restoration would require a double-exon skipping of both exons flanking the deletion. Myotube cultures from both patients were transfected with a mixture of exon 43- and 44-specific AONs (DL90.3) or exon 45- and 51-specific AONs (DL470.2). The individual AONs (Table 5) were previously highly effective in single-exon skipping. Transfection efficiencies were typically over 80%, as indicated by the number of cells with specific nuclear uptake of the fluorescent AONs. RT-PCR analysis at 24 to 48 hours post-transfection, indeed demonstrated the feasibility of specific double-exon skipping in both samples (FIGS. 6 and 7). This was confirmed by sequence analysis (data not shown). Additional shorter transcript fragments were obtained due to single-exon skipping: in patient DL90.3, exon 44 skipping (FIG. 6), and in patient DL470.2, exon 51 skipping (FIG. 7).

Multi-Exon Skipping

The splicing of exon 44 directly to exon 52 (as induced in DL470.2) generates an in-frame transcript. We hypothesized that by inducing the skipping of the entire stretch of exons in between, i.e., multi-exon skipping, we would induce a BMD-like deletion (45-51) that covers and restores several known, smaller, DMD mutations. This would further enlarge the group of DMD patients that would benefit from one type of frame correction. The feasibility of multi-exon skipping was first shown in human control myotubes that were treated with a mixture of the exon 45- and 51-specific AONs (FIG. 7; KM 109). We then applied it to myotubes from a third DMD patient carrying an exon 48-50 deletion (50685.1). By the AON-induced skipping of the (remaining) stretch of exons in between and including exons 45 and 51, we obtained the anticipated smaller in-frame transcript with exon 44 spliced to exon 52 (FIG. 7).

Double- and Multi-Exon Skipping Using a U-Linked AON Combination

The skipping of more than one exon from one pre-mRNA molecule requires that both AONs are present in the same nucleus, targeting the same molecule. To enlarge this chance, we here studied the feasibility of one combined AON carrying both AONs specific for exons 45 and 51 (h45AON5 and h51AON2) linked by ten uracil nucleotides (Table 5). Following transfection of this "U-linker AON" into myotubes from human control and the DMD patients D1470.2 and 50685.1, RT-PCR analysis demonstrated its efficacy to generate the anticipated in-frame transcript with exon 44 spliced to exon 52 (FIG. 7). This multi-exon skipping occurred specifically and precisely at the exon boundaries as confirmed by sequence analysis (data not shown). In contrast to patient DL 470.2, the U-linker AON was a slightly more efficient than the mixture of AONs in the human control and in patient 50685.1.

Materials and Methods

AONs and Primers

AONs (Table 5) targeting exons 43, 44 and 51 were previously described (Aartsma-Rus, 2002). AONs targeting exon 45 were newly designed (sequences upon request). All AONs contain a 5' fluorescein group (6-FAM), a full-length phosphorothioate backbone and 2'-O-methyl modified ribose molecules (Eurogentec, BE). To avoid interference with the fluorescent signals of the secondary antibodies, unlabelled AONs were used for immuno-histochemical analyses. Primers for RT-PCR analysis (Table 5, sequences available upon request) were synthesized by Eurogentec (BE).

RNA Isolation and RT-PCR Analysis

At 24 to 48 hours post-transfection, total RNA was isolated from the myotube cultures (RNA-Bee RNA isolation solvent, Campro Scientific, NL). 300 ng of total RNA were used for RT-PCR analysis using C. therm. polymerase (Roche Diagnostics, NL) in a 20 µl reaction at 60° C. for 30 minutes, primed with different DMD gene-specific reverse primers (Table 5). Primary PCRs were performed by 20 cycles of 94° C. (40 seconds), 60° C. (40 seconds) and 72° C. (60 seconds). One µl of these reactions was then re-amplified in nested PCRs by 32 cycles of 94° C. (40 seconds), 60° C. (40 seconds) and 72° C. (60 seconds). PCR products were analyzed on 1.5% or 2% agarose gels. For quantification of the transcript products, nested PCRs were performed using 24 cycles. PCR products were analyzed using the DNA 7500 LabChip® Kit and the Agilent 2100 Bioanalyzer (Agilent Technologies, NL).

Sequence Analysis

RT-PCR products were isolated from agarose gels using the QIAquick Gel Extraction Kit (Qiagen). Direct DNA sequencing was carried out by the Leiden Genome Technology Center (LGTC) using the BigDye Terminator Cycle Sequencing Ready Reaction kit (PE Applied Biosystems) and analyzed on an ABI 3700 Sequencer (PE Applied Biosystems).

Example 4

Expression Vectors Encoding a Transcript Comprising an Oligonucleotide of the Invention Due to the defined turnover rate of both the dystrophin pre-mRNA and the AONs, our DMD frame-correction therapy would require repetitive administrations of AONs. In addition, relatively high levels of antisense RNA will be necessary within the nucleus, where transcription and splicing of the dystrophin pre-mRNA occur. Therefore, we have set up a vector system in which specific AON sequences are incorporated into a modified gene. In this example, this embodiment is described for U7 small nuclear RNA (U7snRNA). U7snRNA is the RNA component of the U7 ribonucleoprotein particle (U7snRNP) that is involved in the processing of the 3' end of histone pre-mRNAs. Inherent to its function, U7snRNA is efficiently transported back from the cytoplasm to the nucleus in which it gets subsequently incorporated into very stable U7snRNP complexes. A similar approach was successfully applied in AON-based gene therapy studies on β-thalassemia (53, 54). In these studies, different plasmids were engineered containing a modified U7snRNA gene from which the natural antisense sequence directed to the histone pre-mRNA was replaced with antisense sequences targeted to different β-thalassemia-associated aberrant splicing sites in the β-globin gene. Following transfection of these plasmids, correct splicing and expression of the full-length β-globin protein could be restored with an efficiency of up to 65% in cultured cells expressing the different mutant β-globin genes.

Various U7snRNA gene constructs were engineered as described in reference 53 with the modification that the β-globin sequences were exactly replaced by the antisense sequences derived from the different AONs. In this Example, the sequences were replaced by the antisense sequences of m46AON4, 6, 9, or 11 that were effective in inducing the skipping of mouse exon 46. A sense construct was included as negative control (m46SON6). Following construct validation by sequencing, the plasmids were tested in vitro by transfection into cultured C2C12 mouse myoblasts. The U7snRNA-m46AON6 construct was most efficient.

To enhance delivery of the AON-U7snRNA gene constructs, we have cloned them into recombinant adeno-associated viral (rAAV) vectors. AAV is a single-stranded DNA parvovirus that is non-pathogenic and shows a helper-dependent life cycle. In contrast to other viruses (adenovirus, retrovirus, and herpes simplex virus), rAAV vectors have been demonstrated to be very efficient in transducing mature skeletal muscle. Because application of rAAV in classical DMD "gene addition" studies has been hindered by its restricted packaging limits (<5 kb), we applied rAAV for the efficient delivery of the much smaller U7snRNA antisense constructs (<600 bp) to mature murine skeletal muscle. The rAAV-U7-AON vectors also contain the gene for green fluorescence protein (GFP-cDNA), which allows analysis of transduction efficiencies in muscle post-injection. High titer virus productions were effective in inducing exon skipping.

References (to the general part, excluding Example 2)

1. Hoffman E. P., R. H. Brown Jr., and L. M. Kunkel (1987) Dystrophin: the protein product of the Duchenne muscular dystrophy locus. *Cell* 51:919-928.
2. Hoffman E. P., K. H. Fischbeck, R. H. Brown, M. Johnson, R. Medori, J. D. Loike, J. B. Harris, R. Waterston, M. Brooke, L. Specht, et al. (1988) Characterization of dystrophin in muscle-biopsy specimens from patients with Duchenne's or Becker's muscular dystrophy. *N. Engl. J. Med.* 318:1363-1368.
3. Den Dunnen J. T., P. M. Grootscholten, E. Bakker, L. A. Blonden, H. B. Ginjaar, M. C. Wapenaar, H. M. van Paassen, C. van Broeckhoven, P. L. Pearson, and G. J. van Ommen (1989) Topography of the Duchenne muscular dystrophy (DMD) gene: FIGE and cDNA analysis of 194 cases reveals 115 deletions and 13 duplications. *Am. J. Hum. Genet.* 45:835-847.
4. Koenig M., A. H. Beggs, M. Moyer, S. Scherpf, K. Heindrich, T. Bettecken, G. Meng, C. R. Muller, M. Lindlof, H. Kaariainen, et al. (1989) The molecular basis for Duchenne versus Becker muscular dystrophy: correlation of severity with type of deletion. *Am. J. Hum. Genet.* 45:498-506.
5. Tuffery-Giraud S., S. Chambert, J. Demaille, and M. Claustres (1999) Point mutations in the dystrophin gene: evidence for frequent use of cryptic splice sites as a result of splicing defects. *Hum. Mutat.* 14:359-368.
6. Prior T. W., C. Bartolo, D. K. Pearl, A. C. Papp, P. J. Snyder, M. S. Sedra, A. H. Burghes, and J. R. Mendell (1995) Spectrum of small mutations in the dystrophin coding region. *Am. J. Hum. Genet.* 57:22-33.
7. Moser H. (1984) Duchenne muscular dystrophy: pathogenetic aspects and genetic prevention. *Hum. Genet.* 66:17-40.
8. Emery A. E. (2002) The muscular dystrophies. *Lancet* 359:687-695.
9. Yoshida M. and E. Ozawa (1990) Glycoprotein complex anchoring dystrophin to sarcolemma. *J. Biochem.* (Tokyo), 108:748-752.
10. Ervasti J. M. and K. P. Campbell (1991) Membrane organization of the dystrophin-glycoprotein complex. *Cell* 66:1121-1131.
11. Di Blasi C., L. Morandi, R. Barresi, F. Blasevich, F. Comelio, and M. Mora (1996) Dystrophin-associated protein abnormalities in dystrophin-deficient muscle fibers from symptomatic and asymptomatic Duchenne/Becker muscular dystrophy carriers. *Acta Neuropathol.* (Berl), 92:369-377.
12. Ervasti J. M., K. Ohlendieck, S. D. Kahl, M. G. Gaver, and K. P. Campbell (1990) Deficiency of a glycoprotein component of the dystrophin complex in dystrophic muscle. *Nature* 345:315-319.
13. Matsumura K., A. H. Burghes, M. Mora, F. M. Tome, L. Morandi, F. Cornello, F. Leturcq, M. Jeanpierre, J. C. Kaplan, P. Reinert, et al. (1994) Immunohistochemical analysis of dystrophin-associated proteins in Becker/Duchenne muscular dystrophy with huge in-frame deletions in the NH2-terminal and rod domains of dystrophin. *J. Clin. Invest.* 93:99-105.
14. Monaco A. P., C. J. Bertelson, S. Liechti-Gallati, H. Moser, L. M. Kunkel (1988) An explanation for the phenotypic differences between patients bearing partial deletions of the DMD locus. *Genomics* 2:90-95.
15. Clemens P. R. and F. J. Duncan (2001) Progress in gene therapy for Duchenne muscular dystrophy. *Curr. Neurol. Neurosci. Rep.* 1:89-96.
16. Khan M. A. (1993) Corticosteroid therapy in Duchenne muscular dystrophy. *J. Neurol. Sci.* 120:8-14.

17. De Angelis F. G., O. Sthandier, B. Berarducci, S. Toso, G. Galluzzi, E. Ricci, G. Cossu and I. Bozzoni (2002) Chimeric snRNA molecules carrying antisense sequences against the splice junctions of exon 51 of the dystrophin pre-mRNA induce exon skipping and restoration of a dystrophin synthesis in Delta 48-50 DMD cells. *Proc. Natl. Acad. Sci. USA* 99:9456-9461.

18. Mann C. J., K. Honeyman, A. J. Cheng, T. Ly, F. Lloyd, S. Fletcher, J. E. Morgan, T. A. Partridge and S. D. Wilton (2001) Antisense-induced exon skipping and synthesis of dystrophin in the mdx mouse. *Proc. Natl. Acad. Sci. USA,* 98:42-47.

19. van Deutekom J. C., M. Bremmer-Bout, A. A. Janson, I. B. Ginjaar, F. Baas, J. T. den Dunnen and G. J. van Ommen (2001) Antisense-induced exon skipping restores dystrophin expression in DMD patient-derived muscle cells. *Hum. Mol. Genet.* 10:1547-1554.

20. Wilton S. D., F. Lloyd, K. Carville, S. Fletcher, K. Honeyman, S. Agrawal and R. Kole (1999) Specific removal of the nonsense mutation from the mdx dystrophin mRNA using antisense oligonucleotides. *Neuromuscul. Disord.* 9:330-338.

21. Dunckley M. G., M. Manoharan, P. Villiet, I. C. Eperon and G. Dickson (1998) Modification of splicing in the dystrophin gene in cultured Mdx muscle cells by antisense oligoribonucleotides. *Hum. Mol. Genet.* 7:1083-1090.

22. Takeshima Y., H. Wada, M. Yagi, Y. Ishikawa, R. Minami, H. Nakamura and M. Matsuo (2001) Oligonucleotides against a splicing enhancer sequence led to dystrophin production in muscle cells from a Duchenne muscular dystrophy patient. *Brain Dev.* 23:788-790.

23. Aartsma-Rus A., M. Bremmer-Bout, A. Janson, J. den Dunnen, G. van Ommen and J. van Deutekom (2002) Targeted exon skipping as a potential gene correction therapy for Duchenne muscular dystrophy. *Neuromuscul. Disord.* 12, S71.

24. Shiga N., Y. Takeshima, H. Sakamoto, K. Inoue, Y. Yokota, M. Yokoyama and M. Matsuo (1997) Disruption of the splicing enhancer sequence within exon 27 of the dystrophin gene by a nonsense mutation induces partial skipping of the exon and is responsible for Becker muscular dystrophy. *J. Clin. Invest.* 100:2204-2210.

25. Cartegni L., S. L. Chew and A. R. Krainer (2002) Listening to silence and understanding nonsense: exonic mutations that affect splicing. *Nat. Rev. Genet.* 3:285-298.

26. Schaal T. D. and T. Maniatis (1999) Multiple distinct splicing enhancers in the protein-coding sequences of a constitutively spliced pre-mRNA. *Mol. Cell. Biol.* 19:261-273.

27. Takeshima Y., H. Nishio, H. Sakamoto, H. Nakamura and M. Matsuo (1995) Modulation of in vitro splicing of the upstream intron by modifying an intra-exon sequence which is deleted from the dystrophin gene in dystrophin Kobe. *J. Clin. Invest.* 95:515-520.

28. Pramono Z. A., Y. Takeshima, H. Alimsardjono, A. Ishii, S. Takeda, and M. Matsuo (1996) Induction of exon skipping of the dystrophin transcript in lymphoblastoid cells by transfecting an antisense oligodeoxynucleotide complementary to an exon recognition sequence. *Biochem. Biophys. Res. Commun.* 226:445-449.

29. Koenig M., A. P. Monaco and L. M. Kunkel (1988) The complete sequence of dystrophin predicts a rod-shaped cytoskeletal protein. *Cell* 53:219-226.

30. Den Dunnen J. (1996) The Leiden Muscular Dystrophy pages; http://www.dmd.nl.

31. Mann C. J., K. Honeyman, G. McClorey, S. Fletcher and S. D. Wilton (2002) Improved antisense oligonucleotide-induced exon skipping in the mdx mouse model of muscular dystrophy. *J. Gene Med.* 4:644-654.

32. Kerr T. P., C. A. Sewry, S. A. Robb and R. G. Roberts (2001) Long mutant dystrophins and variable phenotypes: evasion of nonsense-mediated decay? *Hum. Genet.* 109: 402-407.

33. Klein C. J., D. D. Coovert, D. E. Bulman, P. N. Ray, J. R. Mendell and A. H. Burghes (1992) Somatic reversion/suppression in Duchenne muscular dystrophy (DMD): evidence supporting a frame-restoring mechanism in rare dystrophin-positive fibers. *Am. J. Hum. Genet.* 50:950-959.

34. Sherratt T. G., T. Vulliamy, V. Dubowitz, C. A. Sewry and P. N. Strong (1993) Exon skipping and translation in patients with frameshift deletions in the dystrophin gene. *Am. J. Hum. Genet.* 53:1007-1015.

35. Lu Q. L., G. E. Morris, S. D. Wilton, T. Ly, O. V. Artem'yeva, P. Strong and T. A. Partridge (2000) Massive idiosyncratic exon skipping corrects the nonsense mutation in dystrophic mouse muscle and produces functional revertant fibers by clonal expansion. *J. Cell Biol.* 148:985-996.

36. Nicholson L. V., M. A. Johnson, K. M. Bushby and D. Gardner-Medwin (1993) Functional significance of dystrophin-positive fibers in Duchenne muscular dystrophy. *Arch. Dis. Child* 68:632-636.

37. Vainzof M., M. R. Passos-Bueno, R. I. Takata, C. Pavanello Rde and M. Zatz (1993) Intrafamilial variability in dystrophin abundance correlated with difference in the severity of the phenotype. *J. Neurol. Sci.* 119:38-42.

38. Singh V., S. Sinha, M. Mishra, L. S. Chaturvedi, S. Pradhan, R. D. Mittal and B. Mittal (1997) Proportion and pattern of dystrophin gene deletions in north Indian Duchenne and Becker muscular dystrophy patients. *Hum. Genet.* 99:206-208.

39. Melacini P., M. Fanin, G. A. Danieli, G. Fasoli, C. Villanova, C. Angelini, L. Vitiello, M. Miorelli, G. F. Buja, M. L. Mostacciuolo, et al. (1993) Cardiac involvement in Becker muscular dystrophy. *J. Am. Coll. Cardiol.* 22:1927-1934.

40. Melis M. A., M. Cau, F. Muntoni, A. Mateddu, R. Galanello, L. Boccone, F. Deidda, D. Loi and A. Cao (1998) Elevation of serum creatine kinase as the only manifestation of an intragenic deletion of the dystrophin gene in three unrelated families. *Europ. J. Paediatr. Neurol.* 2:255-261.

41. Onengut, S., G. N. Kavaslar, E. Battaloglu, P. Serdaroglu, F. Deymeer, C. Ozdemir, F. Calafell and A. Tolun (2000) Deletion pattern in the dystrophin gene in Turks and a comparison with Europeans and Indians. *Ann. Hum. Genet.* 64:33-40.

42. Rosenberg C., L. Navajas, D. F. Vagenas, E. Bakker, M. Vainzof, M. R. Passos-Bueno, R. I. Takata, G. J. Van Ommen, M. Zatz and J. T. Den Dunnen (1998) Clinical diagnosis of heterozygous dystrophin gene deletions by fluorescence in situ hybridization. *Neuromuscul. Disord.* 8:447-452.

43. Sertic J., N. Barisic, M. Sostarko, Z. Brzovic and A. Stavljenic-Rukavina (1997) Deletion screening of the Duchenne/Becker muscular dystrophy gene in Croatian population. *Coll. Anthropol.* 21:151-156.

44. Rando T. A. and H. M. Blau (1994) Primary mouse myoblast purification, characterization, and transplantation for cell-mediated gene therapy. *J. Cell Biol.* 125:1275-1287.

45. Murry C. E., M. A. Kay, T. Bartosek, S. D. Hauschka and S. M. Schwartz (1996) Muscle differentiation during repair of myocardial necrosis in rats via gene transfer with MyoD. *J. Clin. Invest.* 98:2209-2217.

46. Roest P. A., A. C. van der Tuijn, H. B. Ginjaar, R. C. Hoeben, F. B. Hoger-Vorst, E. Bakker, J. T. den Dunnen and G. J. van Ommen (1996) Application of in vitro Myo-differentiation of non-muscle cells to enhance gene expression and facilitate analysis of muscle proteins. *Neuromuscul. Disord.* 6:195-202.
47. Havenga M. J., A. A. Lemckert, O. J. Ophorst, M. van Meijer, W. T. Germeraad, J. Grimbergen, M. A. van Den Doel, R. Vogels, J. van Deutekom and A. A. Janson, et al. (2002) Exploiting the natural diversity in adenovirus tropism for therapy and prevention of disease. *J. Virol.* 76:4612-4620.
48. Anderson L. V. and K. Davison (1999) Multiplex Western blotting system for the analysis of muscular dystrophy proteins. *Am. J. Pathol.* 154:1017-1022.
49. Neugebauer K. M. et al., *J. Cell. Biol.* 129:899-908 (1995).
50. Tacke R. and J. L. Manley, *Proc. Soc. Exp. Biol. Med.* 220:59-63 (1999).
51. Graveley B. R. et al., *Curr. Biol.* 9:R6-7 (1999).
52. Misteli T et al., *Nature* 387:523-527 (1997).
53. Gorman L, Suter D, Emerick V, et al. Stable alteration of pre mRNA splicing patterns by modified U7 small nuclear RNAs. *Proc. Natl. Acad. Sci. USA* 1998, 4929-4934.
54. Suter D, Tomasini R, Reber U, et al. Double target antisense U7 snRNAs promote efficient skipping of an aberrant exon in three human beta thalassemic mutations. *Hum. Mol. Genet.* 1999, 8:2415-2423.

TABLE 1

Overview of the patients, the AONs and the primer sets used in this study

| Patients | Mutations | Targeted exons | AONs[a] | RT-primers[b] | Primary PCR sets[b] | Nested PCR sets[b] |
|---|---|---|---|---|---|---|
| DL 515.2 | Deletion exon 45-50 | Exon 51 | h51AON1 | h53r | h41f-h53r | h42f-h52r |
| DL 363.2 | Deletion exon 45-54 | Exon 44 | h44AON1 | h55r2 | h42f-h55r2 | h44f-h55r |
| 50685.1 | Deletion exon 48-50 | Exon 51 | h51AON1 | h53r | h46f-h53r | h47f-h52r |
| DL 589.2 | Deletion exon 51-55 | Exon 50 | h50AON1 | h58r | h47f-h58r | h49f-h57r |
| 53914.1 | Deletion exon 52 | Exon 51 | h51AON1 | h55r | h49f-h55r | h50f-h54r |
|  | " | Exon 53 | h53AON1 | " | " | " |
| 50423.1 | Point mutation exon 49 | Exon 49 | h49AON1 | h52r | h46f-h52r | h47f-h51r |

[a]AON sequences were published previously (23).
[b]Primer sequences available upon request.

TABLE 2

Characteristics of the AONs used to study the targeted skipping of 15 different DMD exons[a]

| SEQ ID NO: | Name | Antisense sequence (5'-3') | Length (bp) | G/C% | U/C% | Exon skip | Transcript |
|---|---|---|---|---|---|---|---|
| 1 | h2AON 1 | cccauuuugugaauguuuucuuuu | 24 | 29 | 75 | + | OF |
| 2 | h2AON 2 | uugugcauuuacccauuuugug | 22 | 36 | 68 | − | OF |
| 3 | h29AON 1 | Uauccucugaaugucgcauc | 20 | 45 | 65 | + | IF |
| 4 | h29AON 2 | gguuauccucugaaugucgc | 20 | 50 | 60 | + | IF |
| 5 | h40AON 1 | Gagccuuuuucuucuuug | 19 | 37 | 79 | + | IF |
| 6 | h40AON 2 | Uccuucgucucugggcuc | 19 | 58 | 79 | + | IF |
| 7 | h41AON 1 | Cuccucuuucuucuucugc | 19 | 47 | 95 | + | IF |
| 8 | h41AON 2 | Cuucgaaacugagcaaauuu | 20 | 35 | 50 | + | IF |
| 9 | h42AON 1 | cuugugagacaugagug | 17 | 47 | 41 | + | IF |
| 10 | h42AON 2 | cagagacuccucuugcuu | 18 | 50 | 67 | + | IF |
| 11 | h43AON 1 | ugcugcugucuucuugcu | 18 | 50 | 78 | − | OF |
| 12 | h43AON 2 | Uuguuaacuuuuucccauu | 19 | 26 | 79 | + | OF |
| 13 | h44AON 1 | cgccgccauuucucaacag | 19 | 58 | 63 | + | OF |
| 14 | h44AON 2 | uuuguauuuagcauguuccc | 20 | 35 | 70 | + | OF |
| 15 | h45AON 1 | gcugaauuauuucuucccc | 19 | 42 | 74 | − | OF |
| 16 | h45AON 5 | gcccaaugccauccugg | 17 | 65 | 58 | + | OF |
| 17 | h46AON 4b | cugcuuccuccaacc | 15 | 60 | 80 | + | OF |
| 18 | h46AON 8b | gcuuuucuuuuaguugcugc | 20 | 40 | 75 | + | OF |

TABLE 2-continued

Characteristics of the AONs used to study the targeted skipping of 15 different DMD exons[a]

| SEQ ID NO: | Name | Antisense sequence (5'-3') | Length (bp) | G/C% | U/C% | Exon skip | Transcript |
|---|---|---|---|---|---|---|---|
| 19 | h47AON 1 | ucuugcucuucugggcuu | 18 | 50 | 78 | − | IF |
| 20 | h47AON 2 | cuugagcuuauuuucaaguuu | 21 | 29 | 67 | − | IF |
| 21 | h48AON 1 | uuucuccuuguuucuc | 16 | 38 | 94 | − | IF |
| 22 | h48AON 2 | ccauaaauuuccaacugauuc | 21 | 33 | 62 | − | IF |
| 23 | h49AON 1 | Cuuccacauccgguuguuu | 19 | 47 | 74 | + | IF |
| 24 | h49AON 2 | Guggcugguuuuuccuugu | 19 | 47 | 68 | + | IF |
| 25 | h50AON 1 | cucagagcucagaucuu | 17 | 47 | 59 | + | OF |
| 26 | h50AON 2 | ggcugcuuugcccuc | 15 | 67 | 73 | − | OF |
| 27 | h51AON 1 | Ucaaggaagauggcauuucu | 20 | 40 | 45 | + | OF |
| 28 | h51AON 2 | ccucugugauuuuauaacuugau | 23 | 30 | 65 | + | OF |
| 29 | h53AON 1 | cuguugccuccgguucug | 18 | 61 | 72 | + | OF |
| 30 | h53AON 2 | uuggcucuggccuguccu | 18 | 61 | 72 | − | OF |

[a]Two AONs were tested per exon. Their different lengths and G/C contents (%) did not correlate to their effectivity in exon skipping (1, induced skipping, 2, no skipping). The AONs were directed to purine (A/G)-rich sequences as indicated by their (antisense) U/C content (%). Skipping of the target exons resulted in either an in-frame (IF) or an out-of-frame (OF) transcript.
[b]van Deutekom et al., 2001 [21].

TABLE 3

Primer sets used for the RT-PCR analyses to detect the skipping of the targeted exons[a]

| Target exon | RT-primer | Primary PCR primer set | Nested PCR primer set |
|---|---|---|---|
| 2 | h4r | h1f1-h4r | h1f2-h3r |
| 2 | h9r | h1f1-h9r | h1f2-h8r |
| 29 | h31r | h25f-h31r | h26f-h30r |
| 40 | h44r | h38f-h44r | h39f-h43r |
| 41 | h44r | h38f-h44r | h39f-h43r |
| 42 | h44r | h38f-h44r | h39f-h43r |
| 43 | h47r | h41f-h47r | h42f-h46r |
| 44 | h47r | h41f-h47r | h42f-h46r |
| 45 | h47r | h41f-h47r | h42f-h46r |
| 46 | h48r | h44f-h48r | h45f-h47r |
| 47 | h52r | h44f-h52r | h46f-h51r |
| 48 | h52r | h44f-h52r | h46f-h51r |
| 49 | h52r | h44f-h52r | h46f-h51r |
| 50 | h52r | h44f-h52r | h46f-h51r |
| 51 | h53r | h47f-h53r | h49f-h52r |
| 53 | h55r | h50f-h55r | h51f-h54r |

[a]Primer sequences are available upon request.

TABLE 4

Overview and frequency of the DMD-causing mutations in the Leiden DMD (LDMD) Database, theoretically correctable by skipping one of the 12 exons successfully targeted in this study

| | Therapeutic for DMD-mutations: | | | | |
|---|---|---|---|---|---|
| Skippable exon | Deletions (exons) (exons) | % of deletions in LDMD Database | Duplications (exons) | % of duplications in LDMD Database | No. of nonsense mutations in LDMD Database |
| 2 | 3-7, 3-19, 3-21 | 2.9 | 2 | 9.0 | |
| 29 | | | | | 5 |
| 40 | | | | | 1 |
| 41 | | | | | 4 |
| 42 | | | | | 0 |

TABLE 4-continued

Overview and frequency of the DMD-causing mutations in the Leiden DMD (LDMD) Database, theoretically correctable by skipping one of the 12 exons successfully targeted in this study

| Skippable exon | Deletions (exons) (exons) | % of deletions in LDMD Database | Duplications (exons) | % of duplications in LDMD Database | No. of nonsense mutations in LDMD Database |
|---|---|---|---|---|---|
| 43 | 44, 44-47, 44-49, 44-51 | 3.7 | 43 | 3.0 | |
| 44 | 5-43, 14-43, 19-43, 30-43, 35-43, 36-43, 40-43, 42-43, 45, 45-54 | 7.8 | 44 | 3.0 | |
| 46 | 21-45, 45, 47-54, 47-56 | 5.6 | | | |
| 49 | | | | | 1 |
| 50 | 51, 51-53, 51-55 | 5.2 | 50 | 3.0 | |
| 51 | 45-50, 47-50, 48-50, 49-50, 50, 52, 52-63 | 17.5 | 51 | 1.5 | |
| 53 | 10-52, 45-52, 46-52, 47-52, 48-52, 49-52, 50-52, 52 | 7.5 | | | |

TABLE 5

Overview of the patients, the AONs and the primer sets used in Example 3

| Patients | Mutations | Targeted exons | AONs | RT-primers[b] | Primary PCR primer sets[b] | Nested PCR primer sets[b] |
|---|---|---|---|---|---|---|
| DL 90.3 | Nonsense mutation exon 43 | Exon 43 | h43AON2[a] | h48r | h41f-h48r | h42f-h47r |
| | | Exon 44 | h44AON1[a] | | | |
| DL470.2 | Deletion exon 46-50 | Exon 45 | h45AON5 | h53r | h42f-h53r | h43-h52r |
| | | Exon 51 | h51AON2[a] | | | |
| | | Exon 45 | U-linker | h53r | h42f-h53r | h43f-h52r |
| | | Exon 51 | AON[c] | | | |

[a]Separate AON sequences were published previously (Aartsma-Rus, 2002).
[b]Primer sequences available upon request.
[c]U linker AON consists of h45AON5 linked to h51AON2 by ten uracils.

What is claimed is:

1. An isolated oligonucleotide of between 20 to 50 nucleotides comprising a sequence consisting of SEQ ID: 27.

2. The isolated oligonucleotide of claim 1, wherein the oligonucleotide comprises a 2'-O-methyl-phosphorothioate oligoribonucleotide modification.

3. The isolated oligonucleotide of claim 1, wherein the oligonucleotide is a peptide nucleic acid, locked nucleic acid, and/or morpholino phosphorodiamidate oligonucleotide.

* * * * *

(12) EX PARTE REEXAMINATION CERTIFICATE (8933rd)
United States Patent
van Deutekom

(10) Number: US 7,534,879 C1
(45) Certificate Issued: *Mar. 27, 2012

(54) MODULATION OF EXONRECOGNITION IN PRE-MRNA BY INTERFERING WITH THE SECONDARY RNA STRUCTURE

(75) Inventor: Judith C. T. van Deutekom, Dordrecht (NL)

(73) Assignee: Academisch Ziekenhuis Leiden, Leiden (NL)

Reexamination Request:
No. 90/011,320, Nov. 9, 2010

Reexamination Certificate for:
Patent No.: 7,534,879
Issued: May 19, 2009
Appl. No.: 12/198,007
Filed: Aug. 25, 2008

( * ) Notice: This patent is subject to a terminal disclaimer.

Related U.S. Application Data

(63) Continuation of application No. 11/233,495, filed on Sep. 21, 2005, which is a continuation of application No. PCT/NL03/00214, filed on Mar. 21, 2003.

(51) Int. Cl.
*C07H 21/04* (2006.01)

(52) U.S. Cl. ............... 536/24.5; 435/325; 435/375; 435/6.11; 435/6.15; 536/24.31

(58) Field of Classification Search ............. 536/24
See application file for complete search history.

(56) References Cited

To view the complete listing of prior art documents cited during the proceeding for Reexamination Control Number 90/011,320, please refer to the USPTO's public Patent Application Information Retrieval (PAIR) system under the Display References tab.

*Primary Examiner* — Sharon Turner

(57) ABSTRACT

The invention provides a method for generating an oligonucleotide with which an exon may be skipped in a pre-mRNA and thus excluded from a produced mRNA thereof. Further provided are methods for altering the secondary structure of an mRNA to interfere with splicing processes and uses of the oligonucleotides and methods in the treatment of disease. Further provided are pharmaceutical compositions and methods and means for inducing skipping of several exons in a pre-mRNA.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-3 is confirmed.

* * * * *